US006774219B2

(12) United States Patent
Hostetter et al.

(10) Patent No.: US 6,774,219 B2
(45) Date of Patent: Aug. 10, 2004

(54) CANDIDA ALBICANS GENE, INTEGRIN-LIKE PROTEIN, ANTIBODIES, AND METHODS OF USE

(75) Inventors: Margaret K. Hostetter, Milford, CT (US); Cheryl A. Gale, Maple Grove, MN (US); Kathleen Kendrick, Columbus, OH (US)

(73) Assignee: Regents of the University of Minnesota, Minneapolis, MN (US)

( * ) Notice: Subject to any disclaimer, the term of this patent is extended or adjusted under 35 U.S.C. 154(b) by 96 days.

(21) Appl. No.: 09/978,343

(22) Filed: Oct. 15, 2001

(65) Prior Publication Data

US 2003/0082680 A1 May 1, 2003

Related U.S. Application Data

(62) Division of application No. 09/264,604, filed on Mar. 8, 1999, now Pat. No. 6,346,411, which is a division of application No. 08/642,846, filed on May 3, 1996, now Pat. No. 5,886,151.

(51) Int. Cl.[7] ......................... C07K 16/14; C07K 16/28
(52) U.S. Cl. ............................... 530/388.5; 530/387.1; 530/387.9; 530/388.1; 530/388.2; 530/389.1; 424/130.1; 424/139.1; 424/141.1; 424/152.1; 424/172.1; 435/255.1; 536/23.74
(58) Field of Search .................... 536/23.74; 424/130.1, 424/139.1, 141.1, 143.1, 156.1, 172.1; 435/255.1; 530/387.9, 388.1, 388.2, 388.22, 388.5, 389.1

(56) References Cited

U.S. PATENT DOCUMENTS

| | | | |
|---|---|---|---|
| 4,542,020 A | 9/1985 | Jackson et al. | |
| 4,661,454 A | 4/1987 | Botstein et al. | |
| 4,670,382 A | 6/1987 | Buckley et al. | |
| 4,735,901 A | 4/1988 | Kurtz et al. | |
| 4,806,465 A | 2/1989 | Buckley et al. | |
| 4,835,098 A | 5/1989 | Orr et al. | |
| 5,139,936 A | 8/1992 | Botstein et al. | |
| 5,332,660 A | 7/1994 | Takeda et al. | |
| 5,886,151 A | 3/1999 | Hostetter et al. | |
| 6,146,824 A | * 11/2000 | Bar-Shavit | |

FOREIGN PATENT DOCUMENTS

CZ 278 840 7/1994

OTHER PUBLICATIONS

Bujdakova et al, Expression and quantification of the iC3b–binding protein in different *Candida albicans* strains and their morphological stages, FEMS Immunol. Med. Microbiol. 18:147–152, 1997.*
Thronton et al. Analysis of the sugar specificity and molecular location of the beta–glucan binding lectin site of complement receptor type 3 (CD11b/CD18), J. Immunol. Feb. 1996. 156: 1235–1246.*

Forsyth et al. Lymphocyte adhesion to *Candida albicans*, Infection and Immunity. Feb. 2002. 70(2):517–527.*
Vetvicka et al. Soluble beta–glucan polysaccharide binding to the lectin site of neurtophil or natural killer cell complement receptor type 3 (CD11b/CD18) generates a primed state of the receptor capable of mediating cytotoxicity of iC3b–opsinzed target.*
Hostetter, M. An integrin–like protein in *Candida albicans*: implications for pathogenesis. Trends in In Microbiology. Jun. 1996. 4(6): 242–246.*
S. Alaei et al., "Isolation and Biochemical Characterization of the iC3b Receptor of *Candida albicans*", *Inf. Immun.*, 61(4), 1395–1399 (1993).
E. Alani et al., "A Method for Gene Disruption That Allows Repeated Use of URA3 Selection in the Construction of Multiply Disrupted Yeast Strains", *Genetics*, 116, 541–545 (1987).
Bendel et al., "Correlation of Adhesion and Pathogenic Potential in Yeast," *Ped. Res.*, 29(4/2), 167A (1991).
Bendel et al., "Distinct Epithelial Adhesins for *C. albicans* and *C. Tropicalis,"* Clin. Res.*, 41(2), 280A (1993).
Bendel et al., "Distinct Mechanisms of Epithelial Adhesion for *Candida albicans* and *Candida tropicalis*", *J. Clin. Invest.*, 92, 1840–1849 (1993).
Bendel et al., "Epithelial Adhesion in Yeast Species: Correlation with Surface Expression of the Integrin Analog", *J. Infec. Dis.*, 171, 1660–1663 (1995).
Bendel et al., "Expression of the iC3b Receptor on Pathogenic and Non–pathogenic Yeasts," *Proceedings of the Second Conference on Candida and Candidiasis*, Philadelphia, PA, Apr. 1990 (Abstract Only).
Bendel et al., "Inhibitory Peptides and Target Proteins for Epithelial Adhesion in Pathogenic *Candida* Species," *Ped. Res.*, 31(4/2), 157A (1992).
Berman et al., "Expression of *C. albicans* INT1 in *S. cerevisiae* induces germ tubes, hyphal growth and yeast adhesion to human epithelial cells," *Yeast Genetics and Human Disease Conference*, Baltimore, MD, Nov. 14–17, 1996 (Abstract and Poster).
M. J. Blacketer et al., "Mutational Analysis of Morphologic Differentiation in *Saccharomyces cerevisiae*", *Genetics*, 140, 1259–1275 (1995).
R.A. Calderone et al., "Identification of C3d Receptors on *Candida albicans*", *Infect. Immun.*, 56(1), 252–258 (1988).
R.A. Calderone, "Molecular Interactions at the Interface of *Candida albicans* and Host Cells", *Arch. of Med. Res.*, 24(3), 275–279 (1993).
R.A. Calderone, "Recognition between *Candida albicans* and host cells", *Trends Microbiol.*, 1, 55–58 (1993).

(List continued on next page.)

Primary Examiner—Elizabeth Kemmerer
Assistant Examiner—Claire M. Kaufman
(74) Attorney, Agent, or Firm—Mueting, Raasch & Gebhardt, P.A.

(57) ABSTRACT

An isolated and purified DNA molecule encoding Candida albicans protein with integrin-like motifs, the protein itself, antibodies thereto, and methods of use, are provided.

37 Claims, 2 Drawing Sheets

OTHER PUBLICATIONS

Carlson et al., "Genotypic and functional analysis of *Candida albicans* strains from mother–infant pairs," *Ped. Res., 35*(4/2), 295A (1994).

R.W. Davis et al., "Rapid DNA Isolations for Enzymatic and Hybridization Analysis", *Methods Enzymol., 65* 404–411 (1980).

Faix et al., "Genotypic Analysis of a Cluster of Systemic *Candida albicans* Infections in a Nicu," *Peds. Res., 37*(4/2), 291A (1995).

W. A. Fonzi et al., "Isogenic Strain Construction and Gene Mapping in *Candida albicans*", *Genetics, 134*, 717–728 (1993).

Frey et al., "Localization and Distribution of IC3B Binding Sites on *Candida albicans*," 88th *Annual Meeting of the American Society for Microbiology*, Miami Beach, FL, May 8–13, 1988, Abstract No. F–29.

C.A. Gale et al., "A *Candida Albicans* Gene with Integrin Motifs Induces Hyphal–Like Structures in *S. Cerevisiae*", *Pediatric Res., 37*(4/2), 174A (1995).

C.A. Gale et al., "A *Candida Albicans* Gene with Integrin Motifs Induces Hyphal–Like Structures in *S. Cerevisiae*", *Pediatric Res., 37*(4), Part II, Abstract No. 1030, and poster presentation (1995).

C. Gale et al., "Cloning and expression of a gene encoding an integrin–like protein in *Candida albicans*", *Proc. Natl. Acad. Sci. USA, 93*, 357–361 (1996).

Gale et al., "Induction of Epithelial Adhesion and Morphologic Switching by a Single Gene from *Candida alibcans*," *Peds. Res., 41*, 119A (1997).

Gale et al., "Linkage of Adhesion, Filamentous Growth, and Virulence in *Candida albicans* to a Single Gene, *INT1*," *Science, 279*, 1355–1358 (1998).

Gale et al., "Monoallelic Disruption of *aINT1* Reduces Antibody Binding, Adhesion, and Germ Tube Formation in *C. Albicans*," *Peds. Res., 39*(4/2), 171A (1996).

C. Gale et al., "Monoallelic Disruption of αINT1 Reduces Antibody Binding, Adhesion, and Germ Tube Formation In *C. Albicans*", *Pediatric Res., 37*(4), Part II, Abstract No. 1014 (1995).

M. A. Ghannoum et al., "Reduced Virulence of *Candida albicans PHR1* Mutants", *Infection and Immunity, 63*(11), 4528–4530 (1995).

Gilmore et al., "A Molecular Marker for Invasive *Candida albicans*," *Abstracts of the XXVI International Conference on Antimicorobial Agents and Chemotherapy (ICAAC)*, p. 231 New York, NY, Oct. 1987.

Gilmore et al., "An iC3b Receptor on *Candida albicans*: Structure, Function, and Correlates for Pathogenicity", *J. Infect. Dis., 157*(1), 38–46 (1988).

Gilmore et al., "Inducible Binding Site for iC3b on Virulent *Candida albicans*," *Clin. Res., 34*(2), 518A (1986).

Gilmore et al., "Structural and Functional Characteristics of an iC3b Receptor on *Candida albicans*," *Abstracts of the ASM Conference on Candida albicans* (May 1987) (Abstract only).

C. J. Gimeno et al., "Unipolar Cell Divisions in the Yeast *S. cerevisiae* Lead to Filamentous Growth: Regulation by Starvation and RAS", *Cell, 68*, 1077–1090 (1992).

J. W. Goodman, "Immunogenicity & antigenic specificty," *Basic and Clinical Immunology*, Stites et al., Eds., Appleton & Lange, Norwalk, CT, pp. 101 and 108 (1991).

Gustafson et al., "Effects of Glucose Upon CR3 Receptors on *Candida Albicans*: Role in Adhesion to Endothelium," *Clin. Res., 37*(2), 430A (1989).

Gustafson et al., "Glucose–Dependent Adhesion of *Candida Albicans* to Human Endothelium," *Clin. Res., 36*(6) 840A (1988).

K.S. Gustafson et al., "Molecular Mimicry in *Candida albicans*", *J. Clin. Invest., 87*, 1896–1902 (1991).

Gustafson et al., "The iC3b Receptor on *Candida albicans* Mediates Adhesion in a Glucose–Dependent Reaction," *Complement and Inflammation, 6*, 339–340 (1989).

F. Heidenreich et al., "*Candida albicans* and *Candida stellatoidea*, in Contrast to Other *Candida* Species, Bind iC3b and C3d but Not C3b", *Infect. Immun., 50*(2), 598–600 (1985).

Herman et al., "Integrin Analogs in Yeast: Implications for Pathogenesis," *Clin. Res., 39*(2), 244A (1991).

Hershowitz, "MAP Kinase Pathways in Yeast: For Mating and More", *Cell, 80*, 187–197 (1995).

D.D. Hickstein et al., "cDNA sequence for the αM subunit of the human neutrophil adherence receptor indicates homology to integrin α subunits", *Proc. Natl. Acad. Sci. USA, 86*, 257–261 (1989).

M.K. Hostetter, "Adhesion and Morphogenesis in *Candida albicans*", *Pediatric Res., 39*(4), 569–573 (1996).

M.K. Hostetter et al., Abstract of *NICHD Grant No. HD008500* (1997–2000).

M.K. Hostetter et al., Abstract of *NIH Grant No. R–01 AI25827* (1990–1996).

M.K. Hostetter et al., "A *Candida albicans* protein shares structure and functional properties with mammalian integrins," *J. Cell Biol.*, (Suppl. O, 14 part A): 164, Abstract No. 216 (1990).

M.K. Hostetter et al., "Adhesins and Ligands Involved in in the Interaction *Candida* spp. with Epithelial and Endothelial Surfaces," *Clinical Microbiology Reviews, 7*(1), 29–42 (1994).

Hostetter et al., "Cloning and Sequencing of cDNA Encoding the iC3b Receptor on *Candida albicans*," *Complement and Inflammation, 6*, 348 (1989).

Hostetter et al., "Integrin Analogs in *Candida Albicans*, Other *Candida* Species and *Saccharomyces cerevisiae*," *J. Cell. Biochem., Suppl. 16F*, 149 (1992).

Hostetter et al., "Structural and Functional Mimicry of CR3 by an iC3B Receptor on *Candida albicans*," *Complement, 4*, 171 (1987).

M.K. Hostetter et al., "The iC3b Receptor on *Candida albicans*: Subcellular Localization and Modulation of Receptor Expression by Glucose", *J. Infect. Dis., 161*(4), 761–768 (1990).

Hostetter et al., "The iC3b Receptor on *Candida albicans*: Subcellular Localization and Modulation of Receptor Expression by Sugars," *Clin. Res., 36*(6), 847A (1988).

C. Hsiao et al., "High–frequency transformation of yeast by plasmids containing the cloned yeast *ARG4* gene", *Proc. Natl. Acad. Sci. USA, 76*(8), 3829–3833 (1979).

R. Hurley, "*Candidal Vaginitis*", *Proc. R. Soc. Med., 70* (Suppl. 4), 1–10 (1970).

H. Ito et al., "Transformation of Intact Yeast Cells Treated with Alkali Cations", *J. Bacteriol, 153*(1), 163–168 (1983).

E. Jakab et al., "Expression of vitronectin and fibronectin binding by *Candida albicans* yeast cells", *APMIS, 101*, 187–193 (1993).

S. Jitsurong et al., "New milk medium for germ tube and chlamydoconidia production by *Candida albicans*", *Mycopathologia*, 123, 95–98 (1993).

M. Johnston et al., "Sequences that Regulate the Divergent GAL1–GAL10 Promoter in *Saccharomyces cerevisiae*", *Molecular and Cellular Biology*, 4(8), 1440–1448 (1984).

E.W. Jones, "Proteinase Mutants of *Saccharomyces cerevisiae*", *Genetics*, 85(1), 23–32 (1977).

A.J. Kingsman et al., "Replication in *Saccharomyces cerevisiae* of Plasmid pBR313 Carrying DNA From the Yeast trpl Region", *Gene*, 7, 141–152 (1979).

S.A. Klotz, "Plasma and Extracellular Matrix Proteins Mediate in the Fate of *Candida albicans* in the Human Host", *Medical Hypotheses*, 42, 328–334 (1994).

S.A. Klotz et al., "Adherence of *Candida albicans* to immobilized extracellular matrix proteins is mediated by calcium–dependent surface glycoproteins", *Microbial Pathogenesis*, 14, 133–147 (1993).

S. A. Klotz et al., "A Fibronectin Receptor on *Candida albicans* Mediates Adherence of the Fungus to Extracellular Matrix", *The Journal of Infectious Diseases*, 163, 604–610 (1991).

J. R. Kohler et al., "*Candida albicans* strains heterozygous and homozygous for mutations in mitogen–activated protein kinase signaling components have defects in hyphal development", *PNAS USA*, 93, 13223–13228 (1996).

M. B. Kurtz, "Integrative Transformation of *Candida albicans*, Using a Cloned *Candida* ADE2 Gene", *Molecular and Cellular Biology*, 6(1), 142–149 (1986).

E. Leberer et al., "Signal transduction through homologs of the Ste20p and Ste7p protein kinases can trigger hyphal formation in the pathogenic fungus *Candida albicans*", *PNAS USA*, 93, 13217–13222 (1996).

H. Liu et al., "Suppression of Hyphal Formation in *Candida albicans* by Mutation of a STE12 Homolog", *Science*, 266, 1723–1726 (1994).

P. A. Maisch et al., "Adherence of *Candida albicans* to a Fibrin–Platelet Matrix Formed In Vitro", *Infection and Immunity*, 27(2), 650–656 (1980).

Meinke et al., "Cloning of *C. Albicans* DNA Encoding an Integrin Analog," *Peds. Res.*, 35(4/2), 187A (1994).

Meinke et al., "Cloning of *C. albicans* DNA encoding an integrin analog," *Pediatric Res.*, 35(4, part 2), 187A, Abstract No. 1106 (1994).

M. Michishita et al., "A Novel Divalent Cation–Binding Site in the A Domain of the β2 Integin CR3 (CD11b/CD18) Is Essential for Ligand Binding", *Cell*, 72, 857–867 (1993).

National Center for Biotechnology Information, National Library of Medicine, National Institutes of Health, GenBank Locus CAU35070 , Accession No. U35070, "*Candida albicans* integrin–like protein alpha Int1p (alpha INT1) gene, complete cds.," [online]. Bethesda, MD [retrieved on Oct. 10, 2001]. Retrieved from the Internet:<URL: http://www.ncbi.nlm.nih.gov/entrez/query.fcgi?cmd=Retrieve&db=nucleotide&list_uids=1144530&dopt=GenBank, 3 pages.

E. Negre et al., "The Collagen Binding Domain of Fibronectin Contains a High Affinity Binding Site for *Candida albicans*", *J. Biol. Chem.*, 269(35), 22039–22045 (1994).

Pollonelli et al., "New strategies in vaccination against fungal infections,"*J. Med. Vet. Mycology*, 32(1), 105–112 (1994).

D. R. Radford et al., "A scanning electronmicroscopy investigation of the structure of colonies of different morphologies produced by phenotypic switching of *Candida albicans*", *J. Med. Microbiol.*, 40, 416–423 (1994).

Rinard et al., "Microbiology department is a 'hot zone' for experts on emerging infectious diseases," *This Thursday*, 6(27), pp. 3–4, Mar. 27, 1997.

R. L. Roberts et al., "Elements of a single MAP kinase cascade in *Saccharomyces cerevisiae* mediate two developmental programs in the same cell type: mating and invasive growth", *Genes & Development*, 8, 2974–2985 (1994).

J. Sambrook et al., *Molecular Cloning: A Laboratory Manual*, Cold Springs Harbor Laboratory Press, Plainview, NY, $2^{nd}$ Ed., 2.108–2.125 (1989).

G. Santoni et al., "*Candida albicans* expresses a fibronectin receptor antigenically related to α5β1 integrin", *Microbiology*, 140, 2971–2979 (1994).

S. M. Saporito–Irwin et al., "*PHR1*, a pH–Regulated Gene of *Candida albicans*, Is Required for Morphogenesis", *Molecular and Cellular Biology*, 15(2), 601–613 (1995).

D.T. Stinchcomb et al., "Isolation and characterisation of a yeast chromosomal replicator", *Nature*, 282, 39–43 (1979).

G. Tronchin et al., "Fungal Cell Adhesion Molecules in *Candida Albicans*", *Eur. J. Epidemiol.*, 7(1), 23–33 (1991).

G. Tschumper et al., "Sequence of a yeast DNA fragment containing a chromosomal replicator and the TRP1 gene", *Gene*, 10, 157–166 (1980).

P. van Solingen et al., "Fusion of Yeast Spheroplasts", *J. Bact.*, 130(2), 946–947 (1977).

T.C. White, "The Integrin β1 Subunit from the Yeast, *Candida Albicans*", Symposium on Molecular Basis of Cellular Adhesion Held at the $19^{th}$ Annual UCLA Symposia on Molecular and Cellular Biology, Steamboat Springs, CO, Jan. 20–26, 1990, *J. Cell. Biochem.*, Suppl. 0, Abstract No. A243.

Yan, S., "Specific Induction of Fibronectin Binding Activity by Hemoglobin in *Candida albicans* Growth in Defined Media," *Infection and Immunity*, 64(8):2930–2935 (Aug. 1996).

\* cited by examiner

ND A LBICANS GENE, INTEGRIN-
LIKE PROTEIN, ANTIBODIES, AND
METHODS OF USE

This application is a divisional of pending U.S. patent application Ser. No. 09/264,604, filed Mar. 8, 1999, now U.S. Pat. No. 6,346,411, which is a divisional of U.S. patent application Ser. No. 08/642,846, filed May 3, 1996, and issued Mar. 23, 1999 as U.S. Pat. No. 5,886,151, both of which are incorporated herein by reference.

STATEMENT OF GOVERNMENT RIGHTS

This invention was made with government support under Grant No. R-01 AI25827, awarded by the National Institutes of Health. The government has certain rights in the present invention.

BACKGROUND OF THE INVENTION

*Candida albicans* is the leading fungal pathogen in normal hosts and in patients with damaged immune systems. In normal hosts, disease caused by *C. albicans* ranges from mild, easily treated, superficial disease (e.g., thrush in newborn infants; paronychia in workers whose hands are immersed in water) to more severe, chronic or recurrent infections (e.g., candidal vaginitis). It is estimated that 5% of women of child-bearing age will suffer from recurrent candidal vaginitis (Hurley, "Trends in candidal vaginitis." *Proc. R. Soc. Med.* 70 (Suppl. 4), 1–8 (1970), and that virtually every woman will experience at least one episode during her reproductive years. Vaginitis is particularly frequent in otherwise normal females with diabetes or a history of prolonged antibiotic or oral contraceptive use. While short-term topical therapy is effective in treating individual episodes of vaginitis, such agents do not prevent recurrences. Thus, even in the normal host, infection with *C. albicans* can occur at epithelial surfaces, and recurrences are not prevented by presently available therapies.

In immunocompromised hosts such as cancer patients, transplant patients, post-operative surgical patients, premature newborns, or HIV-infected people, *C. albicans* ranks as the leading fungal pathogen. In this population, disease ranges from aggressive local infections such as periodontitis, oral ulceration, or esophagitis in HIV-infected patients, to complex and potentially lethal infections of the bloodstream with subsequent dissemination to brain, eye, heart, liver, spleen, kidneys, or bone. Such grave prognoses require more toxic therapy, with attendant consequences from both the underlying infection and the treatment. Here again, the infection typically begins at an epithelial site, evades local defenses, and invades the bloodstream in the face of immunosuppression. Strategies to interrupt candidal adhesion therefore have broad applicability to the prevention of mild but recurrent disease in the normal host and to the reduction of substantial morbidity and mortality in the immunocompromised.

It is well recognized that *C. albicans* adheres to epithelial and endothelial cells in the human host, oftentimes by recognizing proteins of the extracellular matrix called ligands. These ligands include proteins such as fibronectin, vitronectin, fibrinogen, the C3 degradation fragment iC3b, or the shorter C3 degradation fragment C3d. Because recognition of all of these proteins except C3d is dependent upon the amino acid sequence ARGININE-GLYCINE-ASPARTIC ACID or R-G-D, these candidal adhesions are thought to operate like the vertebrate integrins and are called "integrin-like proteins" or "integrin analogs."

Vertebrate integrins are composed of two subunits: an α-subunit and a β-subunit. There are approximately 14 α and 8 βsubunits described to date in vertebrate cells. Using monoclonal or polyclonal antibodies to vertebrate integrins, several investigators have obtained evidence for integrin-like proteins in *C. albicans*: an αM analog, an α5/β1 complex, or a β1 analog. Neither the α5/β1 complex nor the β1 analog has been isolated from *C. albicans* or from any other candidal species, and the responsible genes encoding these "integrin-like proteins" have not been identified.

SUMMARY OF THE INVENTION

The present invention provides an isolated and purified DNA molecule encoding a *Candida albicans* protein with integrin-like motifs that hybridizes to DNA complementary to DNA having SEQ ID NO:1 under the stringency conditions of hybridization in buffer containing 5×SSC, 5×Denhardt's, 0.5% SDS, 1 mg salmon sperm/25 mls of hybridization solution incubated at 65° C. overnight, followed by high stringency washing with 0.2×SSC/0.1 % SDS at 65° C. Preferably, the present invention provides an isolated and purified DNA molecule encoding the *Candida albicans* protein with integrin-like motifs which has the amino acid sequence having SEQ ID NO:2. Preferably, the DNA is genomic DNA which has the nucleotide sequence shown in Table 1 (SEQ ID NO:1).

The present invention also provides a vector and a cell line transformed by an extrachromosomal plasmid containing non-native DNA encoding *Candida albicans* protein with integrin-like motifs (i.e., *C. albicans* integrin-like protein), as described herein. The cell line preferably comprises *S. cerevisiae*. This cell line can be used in a method of delivering a gene product to a subject.

The present invention also provides a *Candida albicans* protein with integrin-like motifs comprising an I domain, two EF-hand divalent cation binding sites, a sequence sufficient to encode a transmembrane domain, an internal RGD tripeptide, and a carboxy-terminal sequence with a single tyrosine residue. As used herein, an "internal" RGD tripeptide means that the RGD sequence is in the Candida protein, not in the vertebrate proteins recognized by integrins. Preferably, the isolated and purified *C. albicans* integrin-like protein has an amino acid sequence which is SEQ ID NO:2. Also provided are isolated and purified peptides, such as those having an amino acid sequence selected from the group consisting of:

```
YLS PTN NNN SKN VSD MDL HLQ NL;     (SEQ ID NO:4)

DWK LED SND GDR EDN DDI SRF EK;     (SEQ ID NO:5)

SKS ANT VRG DDD GLA SA;             (SEQ ID NO:6)

DHL DSF DRS YNH TEQ SI; and         (SEQ ID NO:7)

WIQ NLQ EII YRN RFR RQ.             (SEQ ID NO:8)
```

The invention also provides a vaccine comprising the protein and peptides, either singly or together, described herein as well as an isolated and purified antibodies to the *C. albicans* integrin-like protein and peptides described herein.

The invention also provides a method of inhibiting adhesion of *Candida albicans* to cells (preferably epithelial cells, and more preferably human epithelial cells). The method includes contacting the *Candida albicans* with antibodies to the *Candida albicans* protein with integrin-like motifs (αInt1p) or to fragments thereof as described herein.

DETAILED DESCRIPTION

Figure 1:
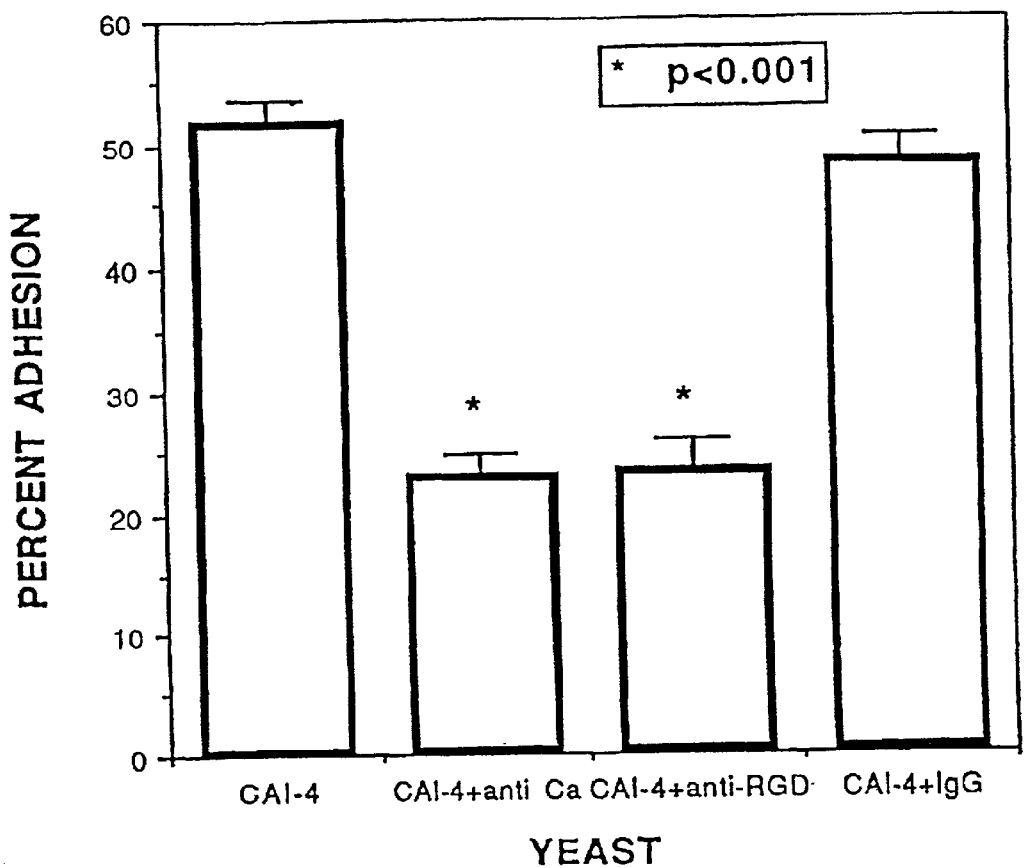
FIG. 1 is a graph of the blockade of candidal adhesion to HeLa cells by antibodies to αInt1p.

Specifically, the present invention is directed to the cloning and expression of a gene (αINT1) for an integrin-like protein (αInt1p) of *Candida albicans*. To that end, the invention provides an isolated and purified DNA molecule encoding a *Candida albicans* protein with an integrin-like motifs or biologically active derivative thereof. More preferably, the DNA is a genomic DNA molecule that encodes the protein represented by the amino acid sequence shown in Table 2 (SEQ ID NO:2). Most preferably, the genomic DNA molecule is represented by the complete nucleotide sequence shown in Table 1 (SEQ ID NO:1). Isolated and purified peptides encoded by this DNA, and derivatives thereof, which are biologically active are also within the scope of the invention.

As used herein, the terms "isolated and purified" refer to in vitro isolation of a DNA molecule or protein from its natural cellular environment, and from association with other coding regions of the *C. albicans* genome, so that it can be sequenced, replicated, and/or expressed. Preferably, the isolated and purified DNA molecules of the invention comprise a single coding region. Thus, the present DNA molecules are those consisting essentially of a DNA segment encoding an integrin-like protein or biologically active derivative thereof. Although the DNA molecule includes a single coding region, it can contain additional nucleotides that do not detrimentally affect the function of the DNA molecule, i.e., the expression of the integrin-like protein or biologically active derivative thereof. For example, the 5' and 3' untranslated regions may contain variable numbers of nucleotides. Preferably, additional nucleotides are outside the single coding region.

The present invention also provides an isolated and purified DNA molecule that encodes integrin-like protein (αInt1p) and that hybridizes to a DNA molecule complementary to the DNA molecule shown in Table 1 (SEQ ID NO:1) under high stringency hybridization conditions. As used herein, "high stringency hybridization conditions" refers to hybridization in buffer containing 5×SSC, 5×Denhardt's, 0.5% SDS, 1 mg salmon sperm/25 mls of hybridization solution incubated at 65° C. overnight, followed by high stringency washing with 0.2×SSC/0.1% SDS at 65° C.

It is envisioned that oligonucleotides are also possible. Oligonucleotide probes and primers are segments of labeled, single-stranded DNA which will hybridize, or noncovalently bind, with complementary single-stranded DNA to be identified.

If desired, the probe and primer can be labeled with any suitable label known to those skilled in the art, including radioactive and nonradioactive labels. Typical radioactive labels include $^{32}P$, $^{125}I$, $^{35}S$, and the like. Nonradioactive labels include, for example, ligands such as biotin or digoxigenin as well as enzymes such as phosphatase or peroxidases, or the various chemiluminescers such as luciferin, or fluorescent compounds like fluorescein and its derivatives. The probe or primer may also be labeled at both ends with different types of labels for ease of separation, as, for example, by using an isotopic label at one end and a biotin label at the other end.

As used herein, the terms "protein with integrin-like motifs" and "integrin-like protein" refer to a candidal adhesin of *C. albicans*, that is expressed at the surface of *C. albicans* and allows candida to bind to epithelial cells, for example. This initial adhesion to epithelium leads to subsequent events in the pathogenesis of invasive candidal infection (e.g., penetration of epithelial barriers and hematogenous dissemination). The unmodified protein (i.e., prior to any post-translational modification) is preferably of about 180–190 kDa, and more preferably of about 188 kDa. It includes several motifs common to αM and αX leukocyte integrins. These motifs include: (1) an Inserted domain ("I" domain) containing a conformationally dependent cation binding site (or MIDAS motif, as disclosed in Michishita et al., *Cell*, 72, 857–867 (1993)); (2) two linear divalent cation binding sites conforming to the EF-hand motif; (3) a sequence sufficient to encode a transmembrane domain; (4) a carboxy-terminal sequence with a single tyrosine residue; and (5) an internal RGD tripeptide (arginine-glycine-aspartic acid). The RGD site is at amino acids 1149–1151 in SEQ ID NO:2.

A "biologically active derivative thereof" is an integrin-like protein that is modified by amino acid deletion, addition, substitution, or truncation, or that has been chemically derivatized, but that nonetheless functions in the same manner as the protein of SEQ ID NO:2. For example, it is known in the art that substitutions of aliphatic amino acids such as alanine, valine and isoleucine with other aliphatic amino acids can often be made without altering the structure or function of a protein. Similarly, substitution of aspartic acid for glutamic acid, in regions other than the active site of an enzyme, are likely to have no appreciable affect on protein structure or function. The term "biologically active derivative" is intended to include *C. albicans* proteins with integrin-like motifs as thus modified. The term also includes fragments, variants, analogs or chemical derivatives thereof. The term "fragment" is meant to refer to any polypeptide subset. Fragments can be prepared by subjecting *C. albicans* proteins with integrin-like motifs to the action of any one of a number of commonly available proteases, such as trypsin, chymotrypsin or pepsin, or to chemical cleavage agents, such as cyanogen bromide. The term "variant" is meant to refer to a molecule substantially similar in structure and function to either the entire *C. albicans* integrin-like protein or to a fragment thereof. A protein or peptide is said to be "substantially similar" if both molecules have substantially similar amino acid sequences, preferably greater than about 80% sequence identity, or if the three-dimensional backbone structures of the molecules are superimposable, regardless of the level of identity between the amino acid sequences. Thus, provided that two molecules possess similar activity, they are considered variants as that term is used herein even if the structure of one of the molecules is not found in the other, or if the sequences of amino acid residues are not identical. The term "analog" is meant to refer to a protein that differs structurally from the wild type *C. albicans* integrin-like protein, but possesses similar activity.

Several fragments of the protein have been prepared and can be used in vaccines or as antigens to prepare anti-peptide antibodies, which can be monoclonal or polyclonal (preferably polyclonal). A 236 amino acid sequence near the amino terminus of the gene product (αInt1p) is shown in Table 3 (SEQ ID NO:3). A 23-mer peptide encompassing the first cation-binding site is YLS PTN NNN SKN VSD MDL HLQ NL (SEQ ID NO:4). A 23-mer peptide encompassing the second divalent cation-binding site is DWK LED SND GDR EDN DDI SRF EK (SEQ ID NO:5). A 17-mer peptide spanning the RGD site and flanking residues is SKS ANT VRG DDD GLA SA (SEQ ID NO:6). A 17-mer peptide from the MIDAS motif of αInt1p is DHL DSF DRS YNH TEQ SI (SEQ ID NO:7). A 17-mer peptide from the C-terminus of αInt1p is WIQ NLQ EII YRN RFR RQ (SEQ ID NO:8).

The antibodies produced to these peptides bind to *C. albicans* blastospores, germ tubes, and hyphae, and thereby block epithelial adhesion of *C. albicans* (i.e., candida). Preferably, the antibodies are able to block *C. albicans* adhesion by at least about 30%, and preferably by at least about 50%. It is believed that this blocking activity of the initial adhesion to epithelium will reduce and even prevent subsequent events in the pathogenesis of invasive candidal infection.

The present invention also provides a vector comprising an isolated and purified DNA molecule encoding *C. albicans* protein with integrin-like motifs or a biologically active derivative thereof, preferably *C. albicans* protein with integrin-like motifs having the amino acid sequence of SEQ ID NO:2. Preferably, the vector includes a sequence encoding the *C. albicans* protein with integrin-like motifs as well as a second DNA segment operably linked to the coding sequence and capable of directing expression of the coding region, such as a promoter region operably linked to the 5' end of the coding DNA sequence. The vector can also include a DNA segment that is a selectable marker gene or a reporter gene as well as upstream untranslated sequence from the *C. albicans* gene.

The present invention also provides a cell line, preferably a *Saccharomyces cerevisiae* yeast strain transformed with an extrachromosomal plasmid containing non-native DNA encoding the *C. albicans* protein with integrin-like motifs. *S. cerevisiae*, also known as brewer's yeast or baker's yeast, typically exhibits a spheriod, yeast-like form and, under certain conditions, can also exhibit a filamentous, mold-like form. The filamentous cells, which are often referred to as pseudohyphal cells, have an elongated morphology. *S. cerevisiae* (preferably haploid *S. cerevisiae*), which is seldom a pathogen, transformed with the open reading frame of αInt1, displays germ tube-like projections referred to herein as "noses." Thus, synthesis of the Candida gene product αInt1p in *S. cerevisiae* induces germ tubes. Furthermore, αInt1p is surface expressed in *S. cerevisiae* and can be recognized by polyclonal antibodies to αInt1p peptides and by monoclonal antibodies to vertebrate integrins. In this way, a generally harmless yeast becomes "sticky" and "nosey."

The *S. cerevisiae* yeast cells transformed by the gene described herein will adhere to epithelial surfaces as a result of expression of the integrin-like gene described herein; however, they will not invade the cells. Thus, "sticky" *S. cerevisiae* may colonize in patients at risk for Candida infection and thereby block the adhesion sites, and reduce or eliminate the opportunity for Candida to adhere, colonize, and invade. Also, the "sticky" *S. cerevisiae* may function as a gene or gene product delivery system. For example, it is envisioned that a phosphate-binding protein could be delivered to the gastrointestinal tract of a patient with chronic renal failure using Saccharomyces transformed by the integrin-like gene and a second plasmid for expression of the phosphate-binding protein. Alternatively, a second plasmid could be used to provide a source of vaccine antigen for gastrointestinal pathogens like cholera. In the genitourinary tract, expression of spermicides by *S. cerevisiae* transformed with the *C. albicans* integrin-like gene on an extrachromosomal plasmid could provide a cheap and infrequent method of contraception. Also, synthesis of protein-based antiretroviral agents could help to reduce transmission of HIV in the birth canal.

1. Isolation of DNA

Several different methods are available for isolating genomic DNA. Most approaches begin with the purification of protein. Purified protein is then subjected to amino acid microsequencing, either directly or after limited cleavage. The partial amino acid sequence that is obtained can be used to design degenerate oligonucleotide probes or primers for use in the generation of unique, nondegenerate nucleotide sequences by polymerase chain reaction (PCR), sequences that can in turn be used as probes for screening genomic DNA libraries. Antibodies raised against purified protein may also be used to isolate DNA clones from expression libraries.

Alternatively, the sequences of DNAs for related proteins (e.g., human integrins) may be used as starting points in a cloning strategy, so-called "cloning by homology". Another way of utilizing sequence information from different species is to take advantage of shorter areas of high sequence homology among related DNAs from different species and to perform PCR to obtain "species-specific" nondegenerate nucleotide sequences. Such a sequence can then be used for library screening or even for direct PCR-based cloning. Detection of the desired DNA can also involve the use of PCR using novel primers.

Alternatively, the region encoding αInt1p may be obtained from a genomic DNA library or by in vitro polynucleotide synthesis from the complete nucleotide acid sequence.

Libraries are screened with appropriate probes designed to identify the genomic DNA of interest. Preferably, for genomic libraries, suitable probes include oligonucleotides that consist of known or suspected portions of the αInt1p genomic DNA from the same or different species; and/or complementary or homologous genomic DNAs or fragments thereof that consist of the same or a similar DNA. For expression libraries (which express the protein), suitable probes include monoclonal or polyclonal antibodies that recognize and specifically bind to the αInt1p protein. Appropriate probes for screening genomic DNA libraries include, but are not limited to, oligonucleotides, genomic DNAs, or fragments thereof that consist of the same or a similar gene, and/or homologous genomic DNAs or fragments thereof. Screening the genomic DNA library with the selected probe may be accomplished using standard procedures.

Screening genomic DNA libraries using synthetic oligonucleotides as probes is a preferred method of practicing this invention. The oligonucleotide sequences selected as probes should be of sufficient length and sufficiently unambiguous to minimize false positives. The actual nucleotide sequence(s) of the probe(s) is usually designed based on regions of the αInt1p genomic DNA that have the least codon redundancy. The oligonucleotides may be degenerate at one or more positions, i.e., two or more different nucleotides may be incorporated into an oligonucleotide at a given position, resulting in multiple synthetic oligonucleotides. The use of degenerate oligonucleotides is of particular importance where a library is screened from a species in which preferential codon usage is not known.

The oligonucleotide can be labeled such that it can be detected upon hybridization to DNA in the library being screened. A preferred method of labeling is to use ATP and polynucleotide kinase to radiolabel the 5' end of the oligonucleotide. However, other methods may be used to label the oligonucleotide, including, but not limited to, biotinylation or enzyme labeling.

Of particular interest is the αInt1 nucleotide sequence that encodes a full-length mRNA transcript, including the complete coding region for the gene product, αInt1p. Nucleic acid containing the complete coding region can be obtained by screening selected genomic DNA libraries using an oligonucleotide encoding the deduced amino acid sequence.

An alternative means to isolate the DNA encoding αInt1p is to use PCR methodology. This method requires the use of oligonucleotide primer probes that will hybridize to the DNA encoding αInt1p. Strategies for selection of PCR primer oligonucleotides are described below.

2. Insertion of DNA into Vector

The nucleic acid containing the αInt1coding region is preferably inserted into a replicable vector for further cloning (amplification of the DNA) or for expression of the gene product. Many vectors are available, and selection of the appropriate vector will depend on: 1) whether it is to be used for DNA amplification or for DNA expression; 2) the size of the nucleic acid to be inserted into the vector; and 3) the host cell to be transformed with the vector. Most expression vectors are "shuttle" vectors, i.e., they are capable of replication in at least one class of organism but can be transfected into another organism for expression. For example, a vector replicates in E. coli and then the same vector is transfected into yeast or mammalian cells for expression even though it is not capable of replicating independently of the host cell chromosome. Each replicable vector contains various structural components depending on its function (amplification of DNA or expression of DNA) and the host cell with which it is compatible. These components are described in detail below.

Construction of suitable vectors employs standard ligation techniques known in the art. Isolated plasmid or DNA fragments are cleaved, tailored, and religated in the form desired to generate the plasmids required. Typically, the ligation mixtures are used to transform E. coli K12 or E. coli XL1 Blue MRF strains 294 (ATCC 31,446) and successful transformants are selected by ampicillin or tetracycline resistance where appropriate. Plasmids from the transformants are prepared, analyzed by restriction endonuclease digestion, and/or sequenced by methods known in the art.

Replicable cloning and expression vector components generally include, but are not limited to, one or more of the following: an origin of replication, one or more marker genes, an enhancer element, a promoter and a transcription termination sequence.

Vector component: origin of replication. Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast and viruses.

Vector component: marker gene. Expression and cloning vectors may contain a marker gene, also termed a selection gene or selectable marker. This gene encodes a protein necessary for the survival or growth of transformed host cells grown in a selective culture medium. Host cells not transformed with the vector containing the selection gene will not survive in the culture medium. Typical selection genes encode proteins that: (a) confer resistance to antibiotics or other toxins, e.g., ampicillin, neomycin, methotrexate, streptomycin or tetracycline; (b) complement auxotrophic deficiencies; or (c) supply critical nutrients not available from complex media, e.g., the gene encoding D-alanine racemase for Bacillus. One example of a selection scheme utilizes a drug to arrest growth of a host cell. Those cells that are successfully transformed with a heterologous gene express a protein conferring drug resistance and thus survive the selection regimen.

A suitable marker gene for use in yeast is URA3 or the TRP1 gene present in the yeast plasmid YRp7 (Stinchcomb et al., Nature, 282, 39 (1979); Kingsman et al., Gene, 7, 141 (1979); or Tschemper et al., Gene, 10, 157 (1980)). The TRP1 gene provides a selection marker for a mutant strain of yeast lacking the ability to grow in tryptophan, for example, ATCC No. 44076 or PEP4-1 (Jones, Genetics, 85, 23 (1977)).

Vector component: promoter. Expression and cloning vectors usually contain a promoter that is recognized by the host organism and is operably linked to the gene. Promoters are untranslated sequences located upstream (5') to the start codon of a structural gene (generally within about 100 to 1000 bp) that control the transcription and translation of a particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. In contrast, constitutive promoters produce a constant level of transcription of the cloned DNA segment.

At this time, a large number of promoters recognized by a variety of potential host cells are well known in the art. Promoters are removed from their source DNA using a restriction enzyme digestion and inserted into the cloning vector using standard molecular biology techniques. Native or heterologous promoters can be used to direct amplification and/or expression of DNA. Heterologous promoters are preferred, as they generally permit greater transcription and higher yields of expressed protein as compared to the native promoter. Well-known promoters suitable for use with prokaryotic hosts include the beta-lactamase and lactose promoter systems, alkaline phosphatase, a tryptophan (trp) promoter system, and hybrid promoters such as the tac promoter. Such promoters can be ligated to the DNA to be expressed using linkers or adapters to supply any required restriction sites. Promoters for use in bacterial systems may contain a Shine-Dalgarno sequence for RNA polymerase binding.

Promoter sequences are known for eukaryotes. Virtually all eukaryotic genes have an AT-rich region located approximately 25 to 30 bp upstream from the site where transcription is initiated Another sequence found 70 to 80 bases upstream from the start of transcription of many genes is the CXCAAT region where X may be any nucleotide. At the 3' end of most eukaryotic genes is an AATAAA sequence that may be a signal for addition of the poly A tail to the 3' end of the coding sequence. All these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Vector component: enhancer element. Transcription of DNA by higher eukaryotes can be increased by inserting an enhancer sequence into the vector. Enhancers are cis-acting elements of DNA, usually having about 10 to 300 bp, that act on a promoter to increase its transcription. Enhancers are relatively orientation-and position-independent, having been found 5' and 3' to the transcription unit, within an intron as well as within the coding sequence itself. Typically, an enhancer from a eukaryotic cell virus will be used. Examples include the SV40 enhancer on the late side of the replication origin, the cytomegalovirus early promoter enhancer, the polyoma enhancer on the late side of the replication origin, and adenovirus enhancers. The enhancer may be spliced into the vector at a position 5' or 3' to the DNA, but is preferably located at a site 5' of the promoter.

Vector component: transcription termination. Expression vectors used in eukaryotic host cells (e.g., yeast, fungi, etc.) can also contain sequences necessary for the termination of transcription and for stabilizing the mRNA. Such sequences are commonly available from the 5' and, occasionally, 3' untranslated regions of eukaryotic or viral DNAs. These regions can contain nucleotide segments transcribed as polyadenylated fragments in the untranslated portion of the mRNA.

The genetically engineered plasmid of the invention can be used to transform a host cell. As discussed above, a particularly desirable host is a eukaryotic microbe such as filamentous fungi or yeast. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*, Kluyveromyces hosts such as, e.g., *K. lactis, K. fragilis, K. bulgaricus, K. thermotolerans*, and *K. marxianus*, yarrowia, *Pichia pastoris, Trichoderma reesia, Neurospora crassa*, and filamentous fungi such as, e.g., Neurospora, Penicillium, Tolypocladium, and Aspergillus hosts such as *A. nidulans*.

4. Transfection and Transformation

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequence are in fact expressed. Numerous methods of transfection are known to the ordinarily skilled artisan, for example, the calcium phosphate precipitation method and electroporation are commonly used. Successful transfection is generally recognized when any indication of the operation of the vector occurs within the host cell.

Transformation means introducing DNA into an organism so that the DNA is replicable, either as an extrachromosomal element or by chromosomal integration. Depending on the host cell used, transformation is done using standard techniques appropriate to such cells. Transformations into yeast are typically carried out according to the method of Van Solingen et al., *J. Bact.*, 130, 946 (1977) and Hsiao et al., *Proc. Natl. Acad. Sci.* (*USA*), 76(8) 3829–3833 (1979). However, other methods for introducing DNA into cells such as by nuclear injection, electroporation, or protoplast fusion may also be used.

5. Cell Culture

Cells used to produce the αInt1 gene product are cultured in suitable media, as described generally in Sambrook et al. Commercially available media such as Hams F10 (Sigma), Minimal Essential Medium (MEM, Sigma), RPMI-1640 (Sigma), and Dulbecco's Modified Eagle's Medium (DMEM, Sigma) are suitable for culturing the host cells. These media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin' drug), trace elements (defined as inorganic compounds usually present at final concentrations in the micromolar range), and glucose, galactose, or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. Induction of cells, to cause expression of the protein, is accomplished using the procedures required by the particular expression system selected.

The invention has been described with reference to various specific and preferred embodiments and will be further described by reference to the following detailed examples. It is understood, however, that there are many extensions, variations and modifications on the basic theme of the present invention beyond that shown in the examples and detailed description, which are within the spirit and scope of the present invention.

EXAMPLES

Isolation of the Gene αInt1 from *Candida albicans*

DNA from spheroplasts of *C. albicans* 10261 (American Type Culture Collection) was isolated according to standard procedures as disclosed in Davis et al., *Methods Enzymol.*, 65, 404–411 (1980), digested with the restriction enzyme Sau3AI, and packaged in λEMBL3 (Stratagene). Preliminary studies confirmed that a 3.5 kbp EcoRI fragment of *C. albicans* DNA hybridized with a 314 bp EcoRI/SmaI DNA fragment derived from the transmembrane domain of human αM as disclosed in Hickstein et al., *Proc. Natl. Acad. Sci. USA*, 86, 257–261, 1989. Primers for amplification of the EcoRI/SmaI αM DNA fragment were as follows:

```
upstream primer:    5' GAATTCAATGCTACCCTCAA;       (SEQ ID NO:9)

downstream primer:  5' CCCGGGGGACCCCCTTCACT.       (SEQ ID NO:10)
```

A library enriched for 3.0–3.8 kbp EcoRI fragments from *C. albicans* was constructed by digestion of genomic DNA with EcoRI and ligation to pBluescript II SK(+). Plasmid minipreparations from a total of 200 colonies were screened by the sib selection technique for hybridization at 50° C. with [$^{32}$P]-labeled PCR product. Five clones were isolated from three successive screenings. Two of the five clones gave reproducible signals after hybridization with a degenerate oligonucleotide encoding a conserved sequence [KVGFFK] in the cytoplasmic domain of αX: 5' AA(AG) GT(CT) GG(AT) TT(CT) TT(CT) AA(AG) 3' (SEQ ID NO:11). Both clones contained a 3.5 kbp EcoRI insert and failed to hybridize with a degenerate oligonucleotide from the *S. cerevisiae* gene USO1:5' GAA AT(ACT) GA(CT) GA(CT) TT(AG) ATG 3' (SEQ ID NO:12).

A 500 bp HindIII subfragment from one of these clones was used to screen 20,000 clones from a library of *C. albicans* 10261 genomic DNA (prepared commercially from *C. albicans* DNA by Stratagene) by the plaque hybridization technique as disclosed in Sambrook et al., *Molecular Cloning: A Laboratory Manual*, Cold Spring Harbor Lab. Press, Plainview, N.Y., 2nd Ed., pp.2.108–2.125 (1989). The largest hybridizing insert, a 10.5 kbp SalI fragment, was isolated by agarose gel electrophoresis, cloned, and sequenced.

Sequence Analysis

Both strands of the 10.5 kbp SalI fragment were sequenced by the method of gene walking on an Applied Biosystems Model 373 Automated Sequencer in the University of Minnesota Microchemical Facility. Nucleotide and protein sequence analyses were performed with the Genetics Computer Group (U. of WI, Madison) Sequence Analysis Software Package, version 7.0. The nucleotide sequence of the coding strand plus approximately 100 upstream nucleotides and 100 nucleotides of 3' untranslated sequence and the derived amino acid sequence (GenBank Acc. No. U35070) are shown in Tables 1 (SEQ ID NO:1) and 2 (SEQ ID NO:2), respectively. By Southern blot analysis under conditions of high stringency (hybridization at 65° C., final wash in 0.2×SSC/0.1% SDS at 65° C.), this gene is present only in *C. albicans* and not in strains of *C. tropicalis, C. krusei, C. glabrata*, or *S. cerevisiae*.

TABLE 1

```
   1 cccaaaaaag ataaaataaa aacaaaacaa aacaaaagta ctaacaaatt attgaaactt
  61 ttaattttta ataaagaatc agtagatcta ttgttaaaag aaatgaactc aactccaagt
 121 aaattattac cgatagataa acattctcat ttacaattac agcctcaatc gtcctcggca
 181 tcaatattta attccccaac aaaaccattg aatttcccca gaacaaattc caagccgagt
 241 ttagatccaa attcaagctc tgatacctac actagcgaac aagatcaaga gaaagggaaa
 301 gaagagaaaa aggacacagc ctttcaaaca tcttttgata gaaattttga tcttgataat
 361 tcaatcgata tacaacaaac aattcaacat cagcaacaac agccacaaca acaacaacaa
 421 ctctcacaaa ccgacaataa tttaattgat gaattttctt ttcaaacacc gatgacttcg
 481 actttagacc taaccaagca aaatccaact gtggacaaag tgaatgaaaa tcatgcacca
 541 acttatataa atacctcccc caacaaatca ataatgaaaa aggcaactcc taaagcgtca
 601 cctaaaaaag ttgcatttac tgtaactaat cccgaaattc atcattatcc agataataga
 661 gtcgaggaag aagatcaaag tcaacaaaaa gaagattcag ttgagccacc cttaatacaa
 721 catcaatgga aagatccttc tcaattcaat tattctgatg aagatacaaa tgcttcagtt
 781 ccaccaacac caccacttca tacgacgaaa cctacttttg cgcaattatt gaacaaaaac
 841 aacgaagtca atctggaacc agaggcattg acagatatga aattaaagcg cgaaaatttc
 901 agcaatttat cattagatga aaaagtcaat ttatatctta gtcccactaa taataacaat
 961 agtaagaatg tgtcagatat ggatctgcat ttacaaaact tgcaagacgc ttcgaaaaac
1021 aaaactaatg aaaatattca caatttgtca tttgctttaa aagcaccaaa gaatgatatt
1081 gaaaacccat taaactcatt gactaacgca gatattctgt taagatcatc tggatcatca
1141 caatcgtcat tacaatcttt gaggaatgac aatcgtgtct tggaatcagt gcctgggtca
1201 cctaagaagg ttaatcctgg attgtctttg aatgacggca taaagggtt ctctgatgag
1261 gttgttgaat cattacttcc tcgtgactta tctcgagaca aattagagac tacaaaagaa
1321 catgatgcac cagaacacaa caatgagaat tttattgatg ctaaatcgac taataccaat
1381 aagggacaac tcttagtatc atctgatgat catttggact cttttgatag atcctataac
1441 cacactgaac aatcaattt gaatcttttg aatagtgcat cacaatctca aatttcgtta
1501 aatgcattgg aaaaacaaag gcaaacacag gaacaagaac aaacacaagc ggcagagcct
1561 gaagaagaaa cttcgtttag tgataatatc aaagttaaac aagagccaaa gagcaatttg
1621 gagtttgtca aggttaccat caagaaagaa ccagttctgg ccacggaaat aaaagctcca
1681 aaaagagaat tttcaagtcg aatattaaga ataaaaaatg aagatgaaat tgccgaacca
1741 gctgatattc atcctaaaaa agaaaatgaa gcaaacagtc atgtcgaaga tactgatgca
```

TABLE 1-continued

```
1801 ttgttgaaga aagcacttaa tgatgatgag gaatctgaca cgacccaaaa ctcaacgaaa
1861 atgtcaattc gttttcatat tgatagtgat tggaaattgg aagacagtaa tgatggcgat
1921 agagaagata atgatgatat ttctcgtttt gagaaatcag atattttgaa cgacgtatca
1981 cagacttctg atattattgg tgacaaatat ggaaactcat caagtgaaat aaccaccaaa
2041 acattagcac ccccaagatc ggacaacaat gacaaggaga attctaaatc tttggaagat
2101 ccagctaata atgaatcatt gcaacaacaa ttggaggtac cgcatacaaa agaagatgat
2161 agcattttag ccaactcgtc caatattgct ccacctgaag aattgacttt gcccgtagtg
2221 gaagcaaatg attattcatc ttttaatgac gtgaccaaaa cttttgatgc atactcaagc
2281 tttgaagagt cattatctag agagcacgaa actgattcaa aaccaattaa tttcatatca
2341 atttggcata acaagaaaa gcagaagaaa catcaaattc ataaagttcc aactaaacag
2401 atcattgcta gttatcaaca atacaaaaac gaacaagaat ctcgtgttac tagtgataaa
2461 gtgaaaatcc caaatgccat acaattcaag aaattcaaag aggtaaatgt catgtcaaga
2521 agagttgtta gtccagacat ggatgatttg aatgtatctc aattttttacc agaattatct
2581 gaagactctg gatttaaaga tttgaatttt gccaactact ccaataacac caacagacca
2641 agaagtttta ctccattgag cactaaaaat gtcttgtcga atattgataa cgatcctaat
2701 gttgttgaac ctcctgaacc gaaatcatat gctgaaatta gaaatgctag acggttatca
2761 gctaataagg cagcgccaaa tcaggcacca ccattgccac cacaacgaca accatcttca
2821 actcgttcca attcaaataa acgagtgtcc agatttagag tgcccacatt tgaaattaga
2881 agaacttctt cagcattagc accttgtgac atgtataatg atattttga tgatttcggt
2941 gcgggttcta aaccaactat aaaggcagaa ggaatgaaaa cattgccaag tatggataaa
3001 gatgatgtca agaggatttt gaatgcaaag aaaggtgtga ctcaagatga atatataaat
3061 gccaaacttg ttgatcaaaa acctaaaaag aattcaattg tcaccgatcc cgaagaccga
3121 tatgaagaat acaacaaac tgcctctata cacaatgcca ccattgattc aagtatttat
3181 ggccgaccag actccatttc taccgacatg ttgccttatc ttagtgatga attgaaaaaa
3241 ccacctacgg ctttattatc tgctgatcgt ttgtttatgg aacaagaagt acatccgtta
3301 agatcaaact ctgttttggt tcacccaggg gcaggagcag caactaattc ttcaatgtta
3361 ccagagccag attttgaatt aatcaattca cctgctagaa atgtgctgaa caacagtgat
3421 aatgtcgcca tcagtggtaa tgctagtact attagtttta accaattgga tatgaatttt
3481 gatgaccaag ctacaattgg tcaaaaaatc caagagcaac ctgcttcaaa atccgccaat
3541 actgttcgtg gtgatgatga tggattggcc agtgcacctg aaacaccaag aactcctacc
3601 aaaaaggagt ccatatcaag caagcctgcc aagctttctt ctgcctcccc tagaaaatca
3661 ccaattaaga ttggttcacc agttcgagtt attaagaaaa atggatcaat tgctggcatt
3721 gaaccaatcc caaaagccac tcacaaaccg aagaaatcat tccaaggaaa cgagatttca
3781 aaccataaag tacgagatgg tggaatttca ccaagctccg gatcagagca tcaacagcat
3841 aatcctagta tggtttctgt tccttcacag tatactgatg ctacttcaac ggttccagat
3901 gaaaacaaag atgttcaaca caagcctcgt gaaaagcaaa agcaaagcaa tcaccatcgc
3961 catcatcatc atcatcataa acaaaaaact gatattccgg gtgttgttga tgatgaaatt
4021 cctgatgtag gattacaaga acgaggcaaa ttattctttta gagttttagg aattaagaat
4081 atcaatttac ccgatattaa tactcacaaa ggaagattca ctttaacgtt ggataatgga
```

TABLE 1-continued

```
4141 gtgcattgtg ttactacacc agaatacaac atggacgacc ataatgttgc cataggtaaa
4201 gaatttgagt tgacagttgc tgattcatta gagtttattt taactttgaa ggcatcatat
4261 gaaaaacctc gtggtacatt agtagaagtg actgaaaaga aagttgtcaa atcaagaaat
4321 agattgagtc gattatttgg atcgaaagat attatcacca cgacaaagtt tgtgcccact
4381 gaagtcaaag atacctgggc taataagttt gctcctgatg gttcatttgc tagatgttac
4441 attgatttac aacaatttga agaccaaatc accggtaaag catcacagtt tgatctcaat
4501 tgttttaatg aatgggaaac tatgagtaat ggcaatcaac caatgaaaag aggcaaacct
4561 tataagattg ctcaattgga agttaaaatg ttgtatgttc cacgatcaga tccaagagaa
4621 atattaccaa ccagcattag atccgcatat gaaagcatca atgaattaaa caatgaacag
4681 aataattact ttgaaggtta tttacatcaa gaaggaggtg attgtccaat ttttaagaaa
4741 cgttttttca aattaatggg cacttcttta ttggctcata gtgaaatatc tcataaaact
4801 agagccaaaa ttaatttatc aaaagttgtt gatttgattt atgttgataa agaaaacatt
4861 gatcgttcca atcatcgaaa tttcagtgat gtgttattgt tggatcatgc attcaaaatc
4921 aaatttgcta atggtgagtt gattgatttt tgtgctccta ataaacatga aatgaaaata
4981 tggattcaaa atttacaaga aattatctat agaaatcggt tcagacgtca accatgggta
5041 aatttgatgc ttcaacaaca acaacaacaa caacaacaac aaagctccca acagtaattg
5101 aaaggtctac ttttgattt tttaattta attggcaaat atatgcccat tttgtattat
5161 cttttagtct aatagcgttt tcttttttc cagt
```

TABLE 2

```
  1 MNSTPSKLLPIDKHSHLQLQPQSSSASIFNSPTKPLNFPRTNSKPSLDPN
 51 SSSDTYTSEQDQEKGKEEKKDTAFQTSFDRNFDLDNSIDIQQTIQHQQQQ
101 PQQQQQLSQTDNNLIDEFSFQTPMTSTLDLTKQNPTVDKVNENHAPTYIN
151 TSPNKSIMKKATPKASPKKVAFTVTNPEIHHYPDNRVEEEDQSQQKEDSV
201 EPPLIQHQWKDPSQFNYSDEDTNASVPPTPPLHTTKPTFAQLLNKNNEVN
251 SEPEALTDMKLKRENFSNLSLDEKVNLYLSPTNNNNSKNVSDMDSHLQNL
301 QDASKNKTNENIHNLSFALKAPKNDIENPLNSLTNADISLRSSGSSQSSL
351 QSLRNDNRVLESVPGSPKKVNPGLSLNDGIKGFSDEVVESLLPRDLSRDK
401 LETTKEHDAPEHNNENFIDAKSTNTNKGQLLVSSDDHLDSFDRSYNHTEQ
451 SILNLLNSASQSQISLNALEKQRQTQEQEQTQAAEPEEETSFSDNIKVKQ
501 EPKSNLEFVKVTIKKEPVSATEIKAPKREFSSRILRIKNEDEIAEPADIH
551 PKKENEANSHVEDTDALLKKALNDDEESDTTQNSTKMSIRFHIDSDWKLE
601 DSNDGDREDNDDISRFEKSDILNDVSQTSDIIGDKYGNSSSEITTKTLAP
651 PRSDNNDKENSKSLEDPANNESLQQQLEVPHTKEDDSILANSSNIAPPEE
701 LTLPVVEANDYSSFNDVTKTFDAYSSFEESLSREHETDSKPINFISIWHK
751 QEKQKKHQIHKVPTKQIIASYQQYKNEQESRVTSDKVKIPNAIQFKKFKE
801 VNVMSRRVVSPDMDDLNVSQFLPELSEDSGFKDLNFANYSNNTNRPRSFT
851 PLSTKNVLSNIDNDPNVVEPPEPKSYAEIRNARRLSANKAAPNQAPPLPP
901 QRQPSSTRSNSNKRVSRFRVPTFEIRRTSSALAPCDMYNDIFDDFGAGSK
```

TABLE 2-continued

| | |
|---|---|
| 951 | PTIKAEGMKTLPSMDKDDVKRILNAKKGVTQDEYINAKLVDQKPKKNSIV |
| 1001 | TDPEDRYEELQQTASIHNATIDSSIYGRPDSISTDMLPYLSDELKKPPTA |
| 1051 | LLSADRLFMEQEVHPLRSNSVLVHPGAGAATNSSMLPEPDFELINSPARN |
| 1101 | VSNNSDNVAISGNASTISFNQLDMNFDDQATTGQKIQEQPASKSANTVRG |
| 1151 | DDDGLASAPETPRTPTKKESISSKPAKLSSASPRKSPIKIGSPVRVIKKN |
| 1201 | GSIAGIEPIPKATHKPKKSFQGNEISNHKVRDGGISPSSGSEHQQHNPSM |
| 1251 | VSVPSQYTDATSTVPDENKDVQHKPREKQKQKHHHRHHHHHHKQKTDIPG |
| 1301 | VVDDEIPDVGLQERGKLFFRVLGIKNINLPDINTHKGRFTLTLDNGVHCV |
| 1351 | TTPEYNMDDHNVAIGKEFELTVADSLEFILTLKASYEKPRGTLVEVTEKK |
| 1401 | VVKSRNRLSRLFGSKDIITTTKFVPTEVKDTWANKFAPDGSFARCYIDLQ |
| 1451 | QFEDQITGKASQFDLNCFNEWETMSNGNQPMKRGKPYKIAQLEVKMLYVP |
| 1501 | RSDPREILPTSIRSAYESINELNNEQNNYFEGYLHQEGGDCPIFKKRFFK |
| 1551 | LMGTSLLAHSEISHKTRAKINLSKVVDLIYVDKENIDRSNIRNFSDVLLL |
| 1601 | DHAFKIKFANGELIDFCAPNKHEMKIWIQNLQEIIYRNRFRRQPWVNLML |
| 1651 | QQQQQQQQQQSSQQ |

Functional Domains

A 236 amino acid sequence near the amino terminus of the gene product (αInt1p) is shown in Table 3 (SEQ ID NO:3). This sequence, or a portion thereof, is believed to encompass the ligand binding site, or a portion thereof, and would provide very useful antibodies or could be used as a vaccine antigen itself.

TABLE 3

| | |
|---|---|
| | SDEDTNASVPPTPPLHTTKPTFAQLLNKNNEVN |
| 251 | SEPEALTDMKLKRENFSNLSLDEKVNLYLSPTNNNNSKNVSDMDSHLQNL |
| 301 | QDASKNKTNENIHNLSFALKAPKNDIENPLNSLTNADISLRSSGSSQSSL |
| 351 | QSLRNDNRVLESVPGSPKKVNPGLSLNDGIKGFSDEVVESLLPRDLSRDK |
| 401 | LETTKEHDAPEHNNENFIDAKSTNTNKGQLLVSSDDHLDSPDRSYNHTEQ |
| 451 | SIL |

The following peptide sequences were used as antigens for the preparation of anti-peptide polyclonal antibodies in rabbits by commercial contract through Cocalico Biologicals (Reamstown, Pa.). The sequences B–F are listed below and correspond to the protein sequence of αInt1p as reported in GenBank, with the exception of one amino acid substitution in sequence (B), as noted below.

B. A 23-mer peptide encompassing the first cation-binding site. This peptide was synthesized by BioSynthesis Inc. (Lewisville, Tex.). Note that the peptide sequence is MDL, while the GenBank sequence is MDS.

YLS PTN NNN SKN VSD MDL HLQ NL (SEQ ID NO:4)

C. A 23-mer peptide encompassing the second divalent cation-binding site. This peptide was synthesized by Bio-Synthesis Inc. (Lewisville, Tex.).

DWK LED SND GDR EDN DDI SRF EK (SEQ ID NO:5)

D. A 17-mer peptide spanning the RGD site and flanking residues. This peptide was synthesized by the Microchemical Facility of the University of Minnesota.

SKS ANT VRG DDD GLA SA (SEQ ID NO:6)

E. A 17-mer peptide from the MIDAS motif of αInt1p. This peptide was synthesized by the Microchemical Facility of the University of Minnesota.

DHL DSF DRS YNH TEQ SI (SEQ ID NO:7)

F. A 17-mer peptide from the C-terminus of αInt1p. This peptide was synthesized by the Microchemical Facility of the University of Minnesota.

WIQ NLQ EII YRN RFR RQ (SEQ ID NO:8)

Preparation and Evaluation of Antibodies

Polyclonal antibodies were prepared by Cocalico Biologics (Reamstown, Pa.) using the peptides B–F (SEQ ID NOS:4–8) listed above. Generally, each peptide is coupled to an adjuvant, the peptide-adjuvant mixture is injected into rabbits, and the rabbit receives booster injections of the same mixture every three-four weeks. Rabbit serum is withdrawn three weeks after the injections and tested for its titer against the original peptide.

Figure 2:
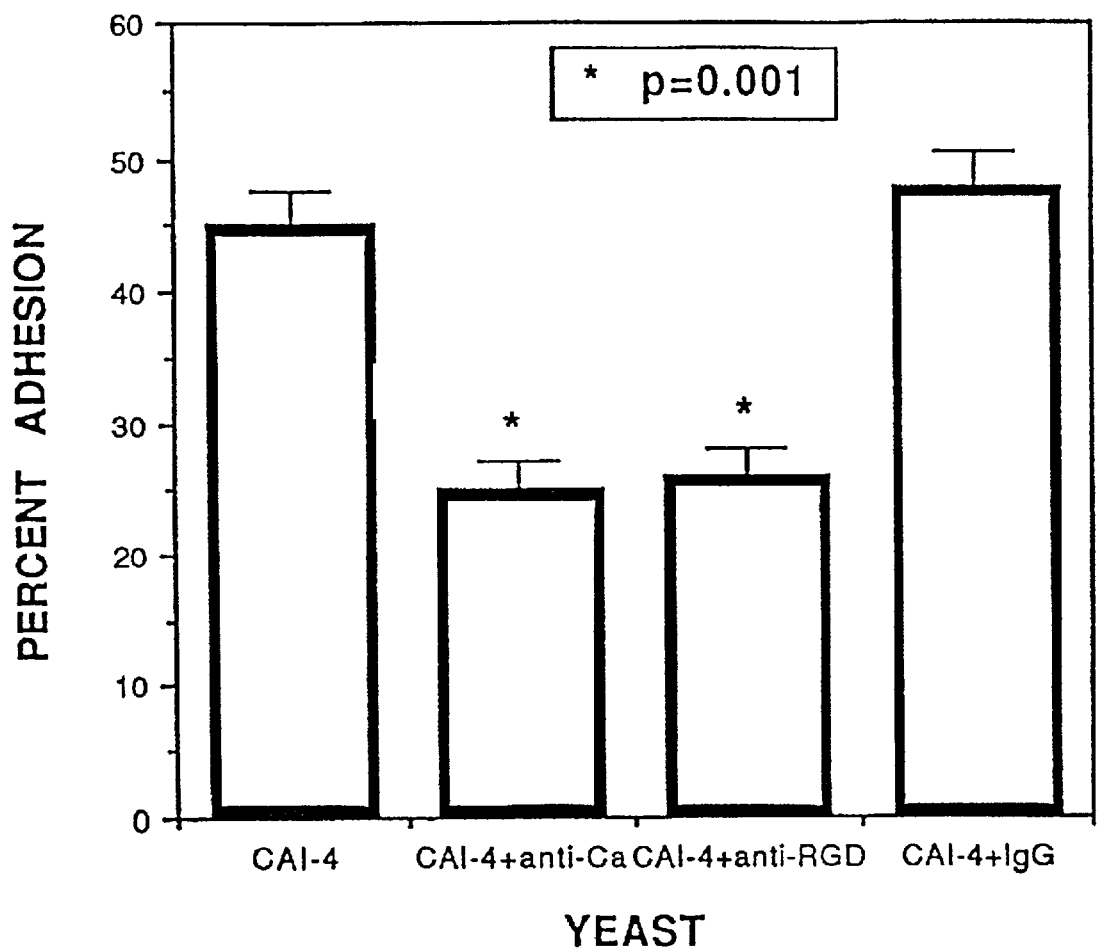
FIG. 2 is a graph of the blockade of candidal adhesion to CHO cells by antibodies to αIntp1.

One rabbit each was used to raise antibodies to each individual peptide. IgG antibodies were purified from the respective rabbit's antiserum by affinity purification on a Protein A-Sepharose column (BioRad) according to standard methods. In FIGS. 1 and 2, anti-Ca denotes antibodies raised to the 23-mer peptide (SEQ ID NO:5) encompassing the second divalent cation binding site; anti-RGD denotes antibodies to the 17-mer peptide encompassing the RGD site and flanking residues (SEQ ID NO:6). CAI-4 denotes the strain of C. albicans that was employed. Anti-Ca or anti-RGD antibodies in a concentration of 1.0 mg/ml were incubated with 1×10⁶[³⁵S]-methionine-labeled C. albicans blastospores for 30 minutes on ice at 4° C. Antibody-coated C. albicans blastospores were then incubated with confluent monolayers of HeLa cells in a 24-well microtiter plate for 60 minutes at 37° C. in 5% $CO_2$, as described in a previous publication (Bendel and Hostetter, Journal of Clinical Investigation, 92, 1840–1849 (1993)). Removal of non-adherent C. alibicans blastospores, release of the HeLa monolayer with attached C. albicans blastospores, counting of the radiolabel, calculation of specific adhesion, and controls for non-specific adhesion were all performed according to the methods in the publication cited above. For FIG. 2, methods remained the same, save that CHO cell monolayers (Chinese hamster ovary cells, a second epithelial cell line) were substituted for HeLa cell monolayers.

FIG. 1 shows that the antibodies against the second divalent cation binding site (SEQ ID NO:5) or the RGD site and flanking residues (SEQ ID NO:6) inhibit binding to HeLa cells by about 50%. FIG. 2 shows that antibodies against the second divalent cation binding site or the RGD site inhibit binding to CHO cells by about 50%.

Induction of αInt1p-Dependent Germ Tubes in Saccharomyces cerevisiae

The entire open reading frame of αInt1 (BglII/SalI fragment) was subcloned into the plasmid pBM272 (obtained from Dr. James Bodley, University of Minnesota) after digestion with BamHI and SalI, in order to place the GAL1–10 promoter upstream of the αInt1 start codon. This plasmid was named pCG01. S. cerevisiae YPH500, obtained from the Yeast Genetic Stock Center (Berkeley, Calif.), was transformed with pBM272 or pCG01 by the lithium acetate procedure as disclosed in Ito et al., J. Bacteriol., 153(1):163–168 (1983). Transformants were selected on agar-based minimal medium (MM=0.17% yeast nitrogen base/0.5% ammonium sulfate) with 2% glucose, in the absence of uracil. Induction of αInt1 was achieved by growing transformants containing pCG01 to mid-exponential phase in non-inducing, non-repressing medium (MM without uracil with 2% raffinose) at 30° C., then harvesting, washing, and resuspending them in inducing medium (MM without uracil with 2% galactose) at 30° C. for the expression of αInt1. YPH500 and YPH500 transformed with vector alone (pBM272) were grown under the identical conditions. S. cerevisiae transformants expressing αInt1p from the plasmid pCG01 made abundant germ tubes after 6 hours' growth in inducing medium.

Applicants hereby incorporate-by-reference into the specification the accompanying Sequence Listing as required by 37 C.F.R. § 1.52(e)(5).

It will be appreciated by those skilled in the art that various modifications can be made to the above described embodiments of the invention without departing from the essential nature thereof. The invention is intended to encompass all such modifications within the scope of the appended claims. All publications, patents, and patent documents are incorporated by reference herein, as though individually incorporated by reference.

What is claimed is:

1. An isolated and purified antibody to a *Candida albicans* integrin-like protein, wherein the protein has an amino acid sequence having SEQ ID NO:2, and wherein the antibody blocks *Candida albicans* adhesion to epithelial and/or endothelial cells.

2. The antibody of claim 1 wherein the antibody is monoclonal or polyclonal.

3. The antibody of claim 1 wherein the antibody blocks *Candida albicans* adhesion to epithelial and/or endothelial cells by at least about 30 percent.

4. The antibody of claim 1 wherein the antibody blocks *Candida albicans* adhesion to epithelial and/or endothelial cells by at least about 50 percent.

5. The antibody of claim 1 wherein the antibody blocks adhesion to epithelial and/or endothelial cells by *Candida albicans* selected from a morphological stage of *Candida albicans* development selected from the group consisting of blastospores, germ tubes, and hyphae.

6. An isolated and purified antibody to a polypeptide, wherein the polypeptide has the amino acid sequence of SEQ ID NO:3, and wherein the antibody blocks *Candida albicans* adhesion to epithelial and/or endothelial cells.

7. The antibody of claim 6 wherein the antibody is monoclonal or polyclonal.

8. The antibody of claim 6, wherein the antibody blocks adhesion to epithelial and/or endotheial cells by *Candida albicans* selected from a morphological stage of *Candida albicans* development selected from the group consisting of blastospores, germ tubes, and hyphae.

9. The antibody of claim 6 wherein the antibody blocks *Candida albicans* adhesion to epithelial and/or endothelial cells by at least about 30 percent.

10. The antibody of claim 6 wherein the antibody blocks *Candida albicans* adhesion to epithelial and/or endothelial cells by at least about 50 percent.

11. An isolated and purified antibody to a polypeptide, wherein the polypeptide consists of SEQ ID NO:3, and wherein the antibody blocks *Candida albicans* adhesion to epithelial and/or endothelial cells.

12. The antibody of claim 11 wherein the antibody is monoclonal or polyclonal.

13. The antibody of claim 11 wherein the antibody blocks *Candida albicans* adhesion to epithelial and/or endothelial cells by at least about 30 percent.

14. The antibody of claim 11 wherein the antibody blocks *Candida albicans* adhesion to epithelial and/or endothelial cells by at least about 50 percent.

15. The antibody of claim 11 wherein the antibody blocks adhesion to epithelial and/or endothelial cells by *Candida albicans* selected from a morphological stage of *Candida albicans* development selected from the group consisting of blastospores, germ tubes, and hyphae.

16. An isolated and purified antibody to a peptide consisting of an amino acid sequence selected from the group consisting of:

(a) YLS PTN NNN SKN VSD MDL HLQ NL (SEQ ID NO:4);

(b) DWK LED SND GDR EDN DDI SRF EK (SEQ ID NO:5);

(c) SKS ANT VRG DDD GLA SA (SEQ ID NO:6);

(d) DHL DSF DRS YNH TEQ SI (SEQ ID NO:7); and (e) WIQ NLQ EII YRN RFR RQ (SEQ ID NO:8).

17. The antibody of claim 16 wherein the antibody is monoclonal or polyclonal.

18. The antibody of claim 16 wherein the antibody blocks *Candida albicans* adhesion to epithelial and/or endothelial cells.

19. The antibody of claim 16 wherein the antibody blocks *Candida albicans* adhesion to epithelial and/or endothelial cells by at least about 30 percent.

20. The antibody of claim 16 wherein the antibody blocks *Candida albicans* adhesion to epithelial and/or endothelial cells by at least about 50 percent.

21. The antibody of claim 16 wherein the antibody blocks adhesion to epithelial and/or endothelial cells by *Candida albicans* selected from a morphological stage of *Candida albicans* development selected from the group consisting of blastospores, germ tubes, and hyphae.

22. An isolated and purified antibody to a peptide having of an amino acid sequence selected from the group consisting of:

(a) YLS PTN NNN SKN VSD MDL HLQ NL (SEQ ID NO:4);

(b) DWK LED SND GDR EDN DDI SRF EK (SEQ ID NO:5);

(c) SKS ANT VRG DDD GLA SA (SEQ ID NO:6);

(d) DHL DSF DRS YNH TEQ SI (SEQ II) NO:7); and (e) WIQ NLQ EII YRN RFR RQ (SEQ ID NO:8), wherein the antibody blocks *Candida albicans* adhesion to epithelial and/or endothelial cells.

23. The antibody of claim 22 wherein the antibody is monoclonal or polyclonal.

24. The antibody of claim 22 wherein the antibody blocks *Candida albicans* adhesion to epithelial and/or endothelial cells by at least about 30 percent.

25. The antibody of claim 22 wherein the antibody blocks *Candida albicans* adhesion to epithelial and/or endothelial cells by at least about 50 percent.

26. The antibody of claim 22 wherein the antibody blocks adhesion to epithelial and/or endothelial cells by *Candida albicans* selected from a morphological stage of *Candida albicans* development selected from the group consisting of blastospores, germ tubes, and hyphae.

27. An isolated and purified antibody to a polypeptide with integrin-like motifs encoded by a polynucleotide that hybridizes to DNA complementary to DNA having SEQ ID NO:1 under stringency conditions of hybridization in buffer containing 5×SSC, 5× Denhardt's, 0.5% SDS, 1 mg salmon sperm/25 mls of hybridization solution incubated at 65° C. overnight, followed by high stringency washing with 0.2× SSC/0.1% SDS at 65° C., wherein the polypeptide with integrin-like motifs contains an I domain, two EF-hand divalent cation binding sites, a sequence sufficient to form a transmembrane domain, an internal RGD tripeptide, and a carboxy-terminal sequence having a single tyrosine residue, and wherein the antibody blocks *Candida albicans* adhesion to epithelial and/or endothelial cells.

28. The antibody of claim 27 wherein the polypeptide comprises an amino acid sequence selected from the group consisting of SEQ ID NO:3, SEQ ID NO:4, SEQ ID NO:5, SEQ ID NO:6, SEQ ID NO:7, and SEQ ID NO:8.

29. The antibody of claim 27 wherein the antibody is monoclonal or polyclonal.

30. The antibody of claim 27 wherein the antibody blocks *Candida albicans* adhesion to epithelial and/or endothelial cells by at least about 30 percent.

31. The antibody of claim 27 wherein the antibody blocks *Candida albicans* adhesion to epithelial and/or endothelial cells by at least about 50 percent.

32. The antibody of claim 27 wherein the antibody blocks adhesion to epithelial and/or endothelial cells by *Candida albicans* selected from a morphological stage of *Candida albicans* development selected from the group consisting of blastospores, germ tubes, and hyphae.

33. An isolated and purified antibody to a *Candida albicans* polypeptide encoded by a polynucleotide having SEQ ID NO:1, wherein the antibody blocks *Candida albicans* adhesion to epithelial and/or endothelial cells.

34. The antibody of claim 33 wherein the antibody is monoclonal or polyclonal.

35. The antibody of claim 33 wherein the antibody blocks *Candida albicans* adhesion to epithelial and/or endothelial cells by at least about 30 percent.

36. The antibody of claim 33 wherein the antibody blocks *Candida albicans* adhesion to epithelial and/or endothelial cells by at least about 50 percent.

37. The antibody of claim 33 wherein the antibody blocks adhesion to epithelial and/or endothelial cells by *Candida albicans* selected from a morphological stage of *Candida albicans* development selected from the group consisting of blastospores, germ tubes, and hyphae.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 5194 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
CCCAAAAAAG ATAAAATAAA AACAAAACAA AACAAAAGTA CTAACAAATT ATTGAAACTT      60

TTAATTTTTA ATAAAGAATC AGTAGATCTA TTGTTAAAAG AAATGAACTC AACTCCAAGT     120

AAATTATTAC CGATAGATAA ACATTCTCAT TTACAATTAC AGCCTCAATC GTCCTCGGCA     180

TCAATATTTA ATTCCCCAAC AAAACCATTG AATTTCCCCA GAACAAATTC CAAGCCGAGT     240

TTAGATCCAA ATTCAAGCTC TGATACCTAC ACTAGCGAAC AAGATCAAGA GAAAGGGAAA     300

GAAGAGAAAA AGGACACAGC CTTTCAAACA TCTTTTGATA GAAATTTTGA TCTTGATAAT     360

TCAATCGATA TACAACAAAC AATTCAACAT CAGCAACAAC AGCCACAACA ACAACAACAA     420

CTCTCACAAA CCGACAATAA TTTAATTGAT GAATTTTCTT TTCAAACACC GATGACTTCG     480

ACTTTAGACC TAACCAAGCA AAATCCAACT GTGGACAAAG TGAATGAAAA TCATGCACCA     540
```

-continued

| | |
|---|---|
| ACTTATATAA ATACCTCCCC CAACAAATCA ATAATGAAAA AGGCAACTCC TAAAGCGTCA | 600 |
| CCTAAAAAAG TTGCATTTAC TGTAACTAAT CCCGAAATTC ATCATTATCC AGATAATAGA | 660 |
| GTCGAGGAAG AAGATCAAAG TCAACAAAAA GAAGATTCAG TTGAGCCACC CTTAATACAA | 720 |
| CATCAATGGA AAGATCCTTC TCAATTCAAT TATTCTGATG AAGATACAAA TGCTTCAGTT | 780 |
| CCACCAACAC CACCCACTTCA TACGACGAAA CCTACTTTTG CGCAATTATT GAACAAAAAC | 840 |
| AACGAAGTCA ATCTGGAACC AGAGGCATTG ACAGATATGA AATTAAAGCG CGAAAATTTC | 900 |
| AGCAATTTAT CATTAGATGA AAAAGTCAAT TTATATCTTA GTCCCACTAA TAATAACAAT | 960 |
| AGTAAGAATG TGTCAGATAT GGATCTGCAT TTACAAAACT TGCAAGACGC TTCGAAAAAC | 1020 |
| AAAACTAATG AAAATATTCA CAATTTGTCA TTTGCTTTAA AAGCACCAAA GAATGATATT | 1080 |
| GAAAACCCAT TAAACTCATT GACTAACGCA GATATTCTGT TAAGATCATC TGGATCATCA | 1140 |
| CAATCGTCAT TACAATCTTT GAGGAATGAC AATCGTGTCT TGGAATCAGT GCCTGGGTCA | 1200 |
| CCTAAGAAGG TTAATCCTGG ATTGTCTTTG AATGACGGCA TAAAGGGGTT CTCTGATGAG | 1260 |
| GTTGTTGAAT CATTACTTCC TCGTGACTTA TCTCGAGACA AATTAGAGAC TACAAAAGAA | 1320 |
| CATGATGCAC CAGAACACAA CAATGAGAAT TTTATTGATG CTAAATCGAC TAATACCAAT | 1380 |
| AAGGGACAAC TCTTAGTATC ATCTGATGAT CATTTGGACT CTTTTGATAG ATCCTATAAC | 1440 |
| CACACTGAAC AATCAATTTT GAATCTTTTG AATAGTGCAT CACAATCTCA AATTTCGTTA | 1500 |
| AATGCATTGG AAAAACAAAG GCAAACACAG GAACAAGAAC AAACACAAGC GGCAGAGCCT | 1560 |
| GAAGAAGAAA CTTCGTTTAG TGATAATATC AAAGTTAAAC AAGAGCCAAA GAGCAATTTG | 1620 |
| GAGTTTGTCA AGGTTACCAT CAAGAAAGAA CCAGTTCTGG CCACGGAAAT AAAAGCTCCA | 1680 |
| AAAAGAGAAT TTTCAAGTCG AATATTAAGA ATAAAAAATG AAGATGAAAT TGCCGAACCA | 1740 |
| GCTGATATTC ATCCTAAAAA AGAAAATGAA GCAAACAGTC ATGTCGAAGA TACTGATGCA | 1800 |
| TTGTTGAAGA AAGCACTTAA TGATGATGAG GAATCTGACA CGACCCAAAA CTCAACGAAA | 1860 |
| ATGTCAATTC GTTTTCATAT TGATAGTGAT TGGAAATTGG AAGACAGTAA TGATGGCGAT | 1920 |
| AGAGAAGATA ATGATGATAT TTCTCGTTTT GAGAAATCAG ATATTTTGAA CGACGTATCA | 1980 |
| CAGACTTCTG ATATTATTGG TGACAAATAT GGAAACTCAT CAAGTGAAAT AACCACCAAA | 2040 |
| ACATTAGCAC CCCCAAGATC GGACAACAAT GACAAGGAGA ATTCTAAATC TTTGGAAGAT | 2100 |
| CCAGCTAATA ATGAATCATT GCAACAACAA TTGGAGGTAC CGCATACAAA AGAAGATGAT | 2160 |
| AGCATTTTAG CCAACTCGTC CAATATTGCT CCACCTGAAG AATTGACTTT GCCCGTAGTG | 2220 |
| GAAGCAAATG ATTATTCATC TTTTAATGAC GTGACCAAAA CTTTTGATGC ATACTCAAGC | 2280 |
| TTTGAAGAGT CATTATCTAG AGAGCACGAA ACTGATTCAA AACCAATTAA TTTCATATAA | 2340 |
| ATTTGGCATA AACAAGAAAA GCAGAAGAAA CATCAAATTC ATAAAGTTCC AACTAAACAG | 2400 |
| ATCATTGCTA GTTATCAACA ATACAAAAAC GAACAAGAAT CTCGTGTTAC TAGTGATAAA | 2460 |
| GTGAAAATCC CAAATGCCAT ACAATTCAAG AAATTCAAAG AGGTAAATGT CATGTCAAGA | 2520 |
| AGAGTTGTTA GTCCAGACAT GGATGATTTG AATGTATCTC AATTTTTACC AGAATTATCT | 2580 |
| GAAGACTCTG GATTTAAAGA TTTGAATTTT GCCAACTACT CCAATAACAC CAACAGACCA | 2640 |
| AGAAGTTTTA CTCCATTGAG CACTAAAAAT GTCTTGTCGA ATATTGATAA CGATCCTAAT | 2700 |
| GTTGTTGAAC CTCCTGAACC GAAATCATAT GCTGAAATTA GAAATGCTAG ACGGTTATCA | 2760 |
| GCTAATAAGG CAGCGCCAAA TCAGGCACCA CCATTGCCAC CACAACGACA ACCATCTTCA | 2820 |
| ACTCGTTCCA ATTCAAATAA ACGAGTGTCC AGATTTAGAG TGCCCACATT TGAAATTAGA | 2880 |
| AGAACTTCTT CAGCATTAGC ACCTTGTGAC ATGTATAATG ATATTTTTGA TGATTTCGGT | 2940 |

```
GCGGGTTCTA AACCAACTAT AAAGGCAGAA GGAATGAAAA CATTGCCAAG TATGGATAAA      3000

GATGATGTCA AGAGGATTTT GAATGCAAAG AAAGGTGTGA CTCAAGATGA ATATATAAAT      3060

GCCAAACTTG TTGATCAAAA ACCTAAAAAG AATTCAATTG TCACCGATCC CGAAGACCGA      3120

TATGAAGAAT TACAACAAAC TGCCTCTATA CACAATGCCA CCATTGATTC AAGTATTTAT      3180

GGCCGACCAG ACTCCATTTC TACCGACATG TTGCCTTATC TTAGTGATGA ATTGAAAAAA      3240

CCACCTACGG CTTTATTATC TGCTGATCGT TTGTTTATGG AACAAGAAGT ACATCCGTTA      3300

AGATCAAACT CTGTTTTGGT TCACCCAGGG GCAGGAGCAG CAACTAATTC TTCAATGTTA      3360

CCAGAGCCAG ATTTTGAATT AATCAATTCA CCTGCTAGAA ATGTGCTGAA CAACAGTGAT      3420

AATGTCGCCA TCAGTGGTAA TGCTAGTACT ATTAGTTTTA ACCAATTGGA TATGAATTTT      3480

GATGACCAAG CTACAATTGG TCAAAAAATC CAAGAGCAAC CTGCTTCAAA ATCCGCCAAT      3540

ACTGTTCGTG GTGATGATGA TGGATTGGCC AGTGCACCTG AAACACCAAG AACTCCTACC      3600

AAAAAGGAGT CCATATCAAG CAAGCCTGCC AAGCTTTCTT CTGCCTCCCC TAGAAAATCA      3660

CCAATTAAGA TTGGTTCACC AGTTCGAGTT ATTAAGAAAA ATGGATCAAT TGCTGGCATT      3720

GAACCAATCC CAAAAGCCAC TCACAAACCG AAGAAATCAT TCCAAGGAAA CGAGATTTCA      3780

AACCATAAAG TACGAGATGG TGGAATTTCA CCAAGCTCCG GATCAGAGCA TCAACAGCAT      3840

AATCCTAGTA TGGTTTCTGT TCCTTCACAG TATACTGATG CTACTTCAAC GGTTCCAGAT      3900

GAAAACAAAG ATGTTCAACA CAAGCCTCGT GAAAAGCAAA AGCAAAAGCA TCACCATCGC      3960

CATCATCATC ATCATCATAA ACAAAAAACT GATATTCCGG GTGTTGTTGA TGATGAAATT      4020

CCTGATGTAG GATTCAAGA ACGAGGCAAA TTATTCTTTA GAGTTTTAGG AATTAAGAAT      4080

ATCAATTTAC CCGATATTAA TACTCACAAA GGAAGATTCA CTTTAACGTT GGATAATGGA      4140

GTGCATTGTG TTACTACACC AGAATACAAC ATGGACGACC ATAATGTTGC CATAGGTAAA      4200

GAATTTGAGT TGACAGTTGC TGATTCATTA GAGTTTATTT TAACTTTGAA GGCATCATAT      4260

GAAAAACCTC GTGGTACATT AGTAGAAGTG ACTGAAAAGA AAGTTGTCAA ATCAAGAAAT      4320

AGATTGAGTC GATTATTTGG ATCGAAAGAT ATTATCACCA CGACAAAGTT TGTGCCCACT      4380

GAAGTCAAAG ATACCTGGGC TAATAAGTTT GCTCCTGATG GTTCATTTGC TAGATGTTAC      4440

ATTGATTTAC AACAATTTGA AGACCAAATC ACCGGTAAAG CATCACAGTT TGATCTCAAT      4500

TGTTTTAATG AATGGGAAAC TATGAGTAAT GGCAATCAAC CAATGAAAAG AGGCAAACCT      4560

TATAAGATTG CTCAATTGGA AGTTAAAATG TTGTATGTTC CACGATCAGA TCCAAGAGAA      4620

ATATTACCAA CCAGCATTAG ATCCGCATAT GAAAGCATCA ATGAATTAAA CAATGAACAG      4680

AATAATTACT TTGAAGGTTA TTTACATCAA GAAGGAGGTG ATTGTCCAAT TTTTAAGAAA      4740

CGTTTTTTCA AATTAATGGG CACTTCTTTA TTGGCTCATA GTGAAATATC TCATAAAACT      4800

AGAGCCAAAA TTAATTTATC AAAAGTTGTT GATTTGATTT ATGTTGATAA AGAAAACATT      4860

GATCGTTCCA ATCATCGAAA TTTCAGTGAT GTGTTATTGT TGGATCATGC ATTCAAAATC      4920

AAATTTGCTA ATGGTGAGTT GATTGATTTT TGTGCTCCTA ATAAACATGA AATGAAAATA      4980

TGGATTCAAA ATTTACAAGA AATTATCTAT AGAAATCGGT TCAGACGTCA ACCATGGGTA      5040

AATTTGATGC TTCAACAACA ACAACAACAA CAACAACACA AAGCTCCCA ACAGTAATTG      5100

AAAGGTCTAC TTTTGATTTT TTAATTTTA ATTGGCAAAT ATATGCCCAT TTTGTATTAT      5160

CTTTTAGTCT AATAGCGTTT TCTTTTTTTC CAGT                                 5194
```

(2) INFORMATION FOR SEQ ID NO: 2:

```
    (i) SEQUENCE CHARACTERISTICS:
        (A) LENGTH: 1664 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Met Asn Ser Thr Pro Ser Lys Leu Leu Pro Ile Asp Lys His Ser His
1               5                   10                  15

Leu Gln Leu Gln Pro Gln Ser Ser Ala Ser Ile Phe Asn Ser Pro
            20                  25                  30

Thr Lys Pro Leu Asn Phe Pro Arg Thr Asn Ser Lys Pro Ser Leu Asp
            35                  40                  45

Pro Asn Ser Ser Ser Asp Thr Tyr Thr Ser Glu Gln Asp Gln Glu Lys
        50                  55                  60

Gly Lys Glu Glu Lys Lys Asp Thr Ala Phe Gln Thr Ser Phe Asp Arg
65                  70                  75                  80

Asn Phe Asp Leu Asp Asn Ser Ile Asp Ile Gln Gln Thr Ile Gln His
                85                  90                  95

Gln Gln Gln Gln Pro Gln Gln Gln Gln Leu Ser Gln Thr Asp Asn
            100                 105                 110

Asn Leu Ile Asp Glu Phe Ser Phe Gln Thr Pro Met Thr Ser Thr Leu
            115                 120                 125

Asp Leu Thr Lys Gln Asn Pro Thr Val Asp Lys Val Asn Glu Asn His
    130                 135                 140

Ala Pro Thr Tyr Ile Asn Thr Ser Pro Asn Lys Ser Ile Met Lys Lys
145                 150                 155                 160

Ala Thr Pro Lys Ala Ser Pro Lys Lys Val Ala Phe Thr Val Thr Asn
                165                 170                 175

Pro Glu Ile His His Tyr Pro Asp Asn Arg Val Glu Glu Asp Gln
            180                 185                 190

Ser Gln Gln Lys Glu Asp Ser Val Glu Pro Pro Leu Ile Gln His Gln
            195                 200                 205

Trp Lys Asp Pro Ser Gln Phe Asn Tyr Ser Asp Glu Asp Thr Asn Ala
    210                 215                 220

Ser Val Pro Pro Thr Pro Leu His Thr Thr Lys Pro Thr Phe Ala
225                 230                 235                 240

Gln Leu Leu Asn Lys Asn Asn Glu Val Asn Ser Glu Pro Glu Ala Leu
                245                 250                 255

Thr Asp Met Lys Leu Lys Arg Glu Asn Phe Ser Asn Leu Ser Leu Asp
            260                 265                 270

Glu Lys Val Asn Leu Tyr Leu Ser Pro Thr Asn Asn Asn Ser Lys
            275                 280                 285

Asn Val Ser Asp Met Asp Ser His Leu Gln Asn Leu Gln Asp Ala Ser
        290                 295                 300

Lys Asn Lys Thr Asn Glu Asn Ile His Asn Leu Ser Phe Ala Leu Lys
305                 310                 315                 320

Ala Pro Lys Asn Asp Ile Glu Asn Pro Leu Asn Ser Leu Thr Asn Ala
                325                 330                 335

Asp Ile Ser Leu Arg Ser Ser Gly Ser Ser Gln Ser Ser Leu Gln Ser
            340                 345                 350

Leu Arg Asn Asp Asn Arg Val Leu Glu Ser Val Pro Gly Ser Pro Lys
            355                 360                 365
```

-continued

Lys Val Asn Pro Gly Leu Ser Leu Asn Asp Gly Ile Lys Gly Phe Ser
370                 375                 380

Asp Glu Val Val Glu Ser Leu Leu Pro Arg Asp Leu Ser Arg Asp Lys
385                 390                 395                 400

Leu Glu Thr Thr Lys Glu His Asp Ala Pro Glu His Asn Asn Glu Asn
            405                 410                 415

Phe Ile Asp Ala Lys Ser Thr Asn Thr Asn Lys Gly Gln Leu Leu Val
            420                 425                 430

Ser Ser Asp Asp His Leu Asp Ser Phe Asp Arg Ser Tyr Asn His Thr
        435                 440                 445

Glu Gln Ser Ile Leu Asn Leu Leu Asn Ser Ala Ser Gln Ser Gln Ile
    450                 455                 460

Ser Leu Asn Ala Leu Glu Lys Gln Arg Gln Thr Gln Glu Gln Glu Gln
465                 470                 475                 480

Thr Gln Ala Ala Glu Pro Glu Glu Thr Ser Phe Ser Asp Asn Ile
            485                 490                 495

Lys Val Lys Gln Glu Pro Lys Ser Asn Leu Glu Phe Val Lys Val Thr
            500                 505                 510

Ile Lys Lys Glu Pro Val Ser Ala Thr Glu Ile Lys Ala Pro Lys Arg
    515                 520                 525

Glu Phe Ser Ser Arg Ile Leu Arg Ile Lys Asn Glu Asp Glu Ile Ala
    530                 535                 540

Glu Pro Ala Asp Ile His Pro Lys Lys Glu Asn Glu Ala Asn Ser His
545                 550                 555                 560

Val Glu Asp Thr Asp Ala Leu Leu Lys Lys Ala Leu Asn Asp Asp Glu
            565                 570                 575

Glu Ser Asp Thr Thr Gln Asn Ser Thr Lys Met Ser Ile Arg Phe His
            580                 585                 590

Ile Asp Ser Asp Trp Lys Leu Glu Asp Ser Asn Asp Gly Asp Arg Glu
        595                 600                 605

Asp Asn Asp Asp Ile Ser Arg Phe Glu Lys Ser Asp Ile Leu Asn Asp
    610                 615                 620

Val Ser Gln Thr Ser Asp Ile Ile Gly Asp Lys Tyr Gly Asn Ser Ser
625                 630                 635                 640

Ser Glu Ile Thr Thr Lys Thr Leu Ala Pro Pro Arg Ser Asp Asn Asn
            645                 650                 655

Asp Lys Glu Asn Ser Lys Ser Leu Glu Asp Pro Ala Asn Asn Glu Ser
            660                 665                 670

Leu Gln Gln Gln Leu Glu Val Pro His Thr Lys Glu Asp Asp Ser Ile
        675                 680                 685

Leu Ala Asn Ser Ser Asn Ile Ala Pro Pro Glu Glu Leu Thr Leu Pro
    690                 695                 700

Val Val Glu Ala Asn Asp Tyr Ser Ser Phe Asn Asp Val Thr Lys Thr
705                 710                 715                 720

Phe Asp Ala Tyr Ser Ser Phe Glu Gly Ser Leu Ser Arg Glu His Glu
            725                 730                 735

Thr Asp Ser Lys Pro Ile Asn Phe Ile Ser Ile Trp His Lys Gln Glu
            740                 745                 750

Lys Gln Lys Lys His Gln Ile His Lys Val Pro Thr Lys Gln Ile Ile
        755                 760                 765

Ala Ser Tyr Gln Gln Tyr Lys Asn Glu Gln Glu Ser Arg Val Thr Ser
770                 775                 780

-continued

```
Asp Lys Val Lys Ile Pro Asn Ala Ile Gln Phe Lys Lys Phe Lys Glu
785                 790                 795                 800

Val Asn Val Met Ser Arg Arg Val Ser Pro Asp Met Asp Asp Leu
                    805                 810                 815

Asn Val Ser Gln Phe Leu Pro Glu Leu Ser Glu Asp Ser Gly Phe Lys
                820                 825                 830

Asp Leu Asn Phe Ala Asn Tyr Ser Asn Asn Thr Asn Arg Pro Arg Ser
            835                 840                 845

Phe Thr Pro Leu Ser Thr Lys Asn Val Leu Ser Asn Ile Asp Asn Asp
        850                 855                 860

Pro Asn Val Val Glu Pro Glu Pro Lys Ser Tyr Ala Glu Ile Arg
865                 870                 875                 880

Asn Ala Arg Arg Leu Ser Ala Asn Lys Ala Ala Pro Asn Gln Ala Pro
                885                 890                 895

Pro Leu Pro Pro Gln Arg Gln Pro Ser Ser Thr Arg Ser Asn Ser Asn
                900                 905                 910

Lys Arg Val Ser Arg Phe Arg Val Pro Thr Phe Glu Ile Arg Arg Thr
            915                 920                 925

Ser Ser Ala Leu Ala Pro Cys Asp Met Tyr Asn Asp Ile Phe Asp Asp
        930                 935                 940

Phe Gly Ala Gly Ser Lys Pro Thr Ile Lys Ala Glu Gly Met Lys Thr
945                 950                 955                 960

Leu Pro Ser Met Asp Lys Asp Val Lys Arg Ile Leu Asn Ala Lys
                965                 970                 975

Lys Gly Val Thr Gln Asp Glu Tyr Ile Asn Ala Lys Leu Val Asp Gln
            980                 985                 990

Lys Pro Lys Lys Asn Ser Ile Val Thr Asp Pro Glu Asp Arg Tyr Glu
        995                 1000                1005

Glu Leu Gln Gln Thr Ala Ser Ile His Asn Ala Thr Ile Asp Ser Ser
    1010                1015                1020

Ile Tyr Gly Arg Pro Asp Ser Ile Ser Thr Asp Met Leu Pro Tyr Leu
1025                1030                1035                1040

Ser Asp Glu Leu Lys Lys Pro Pro Thr Ala Leu Leu Ser Ala Asp Arg
                1045                1050                1055

Leu Phe Met Glu Gln Glu Val His Pro Leu Arg Ser Asn Ser Val Leu
                1060                1065                1070

Val His Pro Gly Ala Gly Ala Ala Thr Asn Ser Ser Met Leu Pro Glu
            1075                1080                1085

Pro Asp Phe Glu Leu Ile Asn Ser Pro Ala Arg Asn Val Ser Asn Asn
        1090                1095                1100

Ser Asp Asn Val Ala Ile Ser Gly Asn Ala Ser Thr Ile Ser Phe Asn
1105                1110                1115                1120

Gln Leu Asp Met Asn Phe Asp Asp Gln Ala Thr Ile Gly Gln Lys Ile
                1125                1130                1135

Gln Glu Gln Pro Ala Ser Lys Ser Ala Asn Thr Val Arg Gly Asp Asp
                1140                1145                1150

Asp Gly Leu Ala Ser Ala Pro Glu Thr Pro Arg Thr Pro Thr Lys Lys
            1155                1160                1165

Glu Ser Ile Ser Ser Lys Pro Ala Lys Leu Ser Ala Ser Pro Arg
    1170                1175                1180

Lys Ser Pro Ile Lys Ile Gly Ser Pro Val Arg Val Ile Lys Lys Asn
1185                1190                1195                1200

Gly Ser Ile Ala Gly Ile Glu Pro Ile Pro Lys Ala Thr His Lys Pro
```

-continued

```
                 1205               1210            1215
Lys Lys Ser Phe Gln Gly Asn Glu Ile Ser Asn His Lys Val Arg Asp
            1220               1225            1230
Gly Gly Ile Ser Pro Ser Ser Gly Ser Glu His Gln Gln His Asn Pro
            1235               1240            1245
Ser Met Val Ser Val Pro Ser Gln Tyr Thr Asp Ala Thr Ser Thr Val
            1250               1255            1260
Pro Asp Glu Asn Lys Asp Val Gln His Lys Pro Arg Glu Lys Gln Lys
1265               1270            1275            1280
Gln Lys His His His Arg His His His His Lys Gln Lys Thr
            1285               1290            1295
Asp Ile Pro Gly Val Val Asp Glu Ile Pro Asp Val Gly Leu Gln
            1300               1305            1310
Glu Arg Gly Lys Leu Phe Phe Arg Val Leu Gly Ile Lys Asn Ile Asn
            1315               1320            1325
Leu Pro Asp Ile Asn Thr His Lys Gly Arg Phe Thr Leu Thr Leu Asp
            1330               1335            1340
Asn Gly Val His Cys Val Thr Thr Pro Glu Tyr Asn Met Asp Asp His
1345               1350            1355            1360
Asn Val Ala Ile Gly Lys Glu Phe Glu Leu Thr Val Ala Asp Ser Leu
            1365               1370            1375
Glu Phe Ile Leu Thr Leu Lys Ala Ser Tyr Glu Lys Pro Arg Gly Thr
            1380               1385            1390
Leu Val Glu Val Thr Glu Lys Lys Val Lys Ser Arg Asn Arg Leu
            1395               1400            1405
Ser Arg Leu Phe Gly Ser Lys Asp Ile Ile Thr Thr Thr Lys Phe Val
            1410               1415            1420
Pro Thr Glu Val Lys Asp Thr Trp Ala Asn Lys Phe Ala Pro Asp Gly
1425               1430            1435            1440
Ser Phe Ala Arg Cys Tyr Ile Asp Leu Gln Gln Phe Glu Asp Gln Ile
            1445               1450            1455
Thr Gly Lys Ala Ser Gln Phe Asp Leu Asn Cys Phe Asn Glu Trp Glu
            1460               1465            1470
Thr Met Ser Asn Gly Asn Gln Pro Met Lys Arg Gly Lys Pro Tyr Lys
            1475               1480            1485
Ile Ala Gln Leu Glu Val Lys Met Leu Tyr Val Pro Arg Ser Asp Pro
            1490               1495            1500
Arg Glu Ile Leu Pro Thr Ser Ile Arg Ser Ala Tyr Glu Ser Ile Asn
1505               1510            1515            1520
Glu Leu Asn Asn Glu Gln Asn Asn Tyr Phe Glu Gly Tyr Leu His Gln
            1525               1530            1535
Glu Gly Gly Asp Cys Pro Ile Phe Lys Lys Arg Phe Lys Leu Met
            1540               1545            1550
Gly Thr Ser Leu Leu Ala His Ser Glu Ile Ser His Lys Thr Arg Ala
            1555               1560            1565
Lys Ile Asn Leu Ser Lys Val Val Asp Leu Ile Tyr Val Asp Lys Glu
            1570               1575            1580
Asn Ile Asp Arg Ser Asn His Arg Asn Phe Ser Asp Val Leu Leu Leu
1585               1590            1595            1600
Asp His Ala Phe Lys Ile Lys Phe Ala Asn Gly Glu Leu Ile Asp Phe
            1605               1610            1615
Cys Ala Pro Asn Lys His Glu Met Lys Ile Trp Ile Gln Asn Leu Gln
            1620               1625            1630
```

```
Glu Ile Ile Tyr Arg Asn Arg Phe Arg Arg Gln Pro Trp Val Asn Leu
        1635                1640                1645

Met Leu Gln Gln Gln Gln Gln Gln Gln Gln Gln Ser Ser Gln Gln
    1650                1655                1660
```

(2) INFORMATION FOR SEQ ID NO: 3:

(i) SEQUENCE CHARACTERISTICS:
        (A) LENGTH: 236 amino acids
        (B) TYPE: amino acid
        (C) STRANDEDNESS: single
        (D) TOPOLOGY: linear (ii) MOLECULE TYPE: protein (ix) FEATURE:
        (D) OTHER INFORMATION: amino acid positions 218-453 from
           SEQ ID NO:2

(xi) SEQUENCE DESCRIPTION: SEQ ID NO: 3:

```
Ser Asp Glu Asp Thr Asn Ala Ser Val Pro Pro Thr Pro Pro Leu His
1               5                   10                  15

Thr Thr Lys Pro Thr Phe Ala Gln Leu Leu Asn Lys Asn Asn Glu Val
            20                  25                  30

Asn Ser Glu Pro Glu Ala Leu Thr Asp Met Lys Leu Lys Arg Glu Asn
            35                  40                  45

Phe Ser Asn Leu Ser Leu Asp Glu Lys Val Asn Leu Tyr Leu Ser Pro
50                  55                  60

Thr Asn Asn Asn Asn Ser Lys Asn Val Ser Asp Met Asp Ser His Leu
65                  70                  75                  80

Gln Asn Leu Gln Asp Ala Ser Lys Asn Lys Thr Asn Glu Asn Ile His
                85                  90                  95

Asn Leu Ser Phe Ala Leu Lys Ala Pro Lys Asn Asp Ile Glu Asn Pro
                100                 105                 110

Leu Asn Ser Leu Thr Asn Ala Asp Ile Ser Leu Arg Ser Ser Gly Ser
            115                 120                 125

Ser Gln Ser Ser Leu Gln Ser Leu Arg Asn Asp Asn Arg Val Leu Glu
        130                 135                 140

Ser Val Pro Gly Ser Pro Lys Lys Val Asn Pro Gly Leu Ser Leu Asn
145                 150                 155                 160

Asp Gly Ile Lys Gly Phe Ser Asp Glu Val Val Glu Ser Leu Leu Pro
                165                 170                 175

Arg Asp Leu Ser Arg Asp Lys Leu Glu Thr Thr Lys Glu His Asp Ala
            180                 185                 190

Pro Glu His Asn Asn Glu Asn Phe Ile Asp Ala Lys Ser Thr Asn Thr
        195                 200                 205

Asn Lys Gly Gln Leu Leu Val Ser Ser Asp Asp His Leu Asp Ser Phe
210                 215                 220

Asp Arg Ser Tyr Asn His Thr Glu Gln Ser Ile Leu
225                 230                 235
```

(2) INFORMATION FOR SEQ ID NO: 4:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide

```
        (xi) SEQUENCE DESCRIPTION: SEQ ID NO: 4:

Tyr Leu Ser Pro Thr Asn Asn Asn Ser Lys Asn Val Ser Asp Met
1               5                   10                  15

Asp Leu His Leu Gln Asn Leu
            20

(2) INFORMATION FOR SEQ ID NO: 5:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Asp Trp Lys Leu Glu Asp Ser Asn Asp Gly Asp Arg Glu Asp Asn Asp
1               5                   10                  15

Asp Ile Ser Arg Phe Glu Lys
            20

(2) INFORMATION FOR SEQ ID NO: 6:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Ser Lys Ser Ala Asn Thr Val Arg Gly Asp Asp Asp Gly Leu Ala Ser
1               5                   10                  15

Ala (2) INFORMATION FOR SEQ ID NO: 7:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Asp His Leu Asp Ser Phe Asp Arg Ser Tyr Asn His Thr Glu Gln Ser
1               5                   10                  15

Ile (2) INFORMATION FOR SEQ ID NO: 8:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Trp Ile Gln Asn Leu Gln Glu Ile Ile Tyr Arg Asn Arg Phe Arg Arg
1               5                   10                  15
```

```
Gln (2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

GAATTCAATG CTACCCTCAA                                              20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CCCGGGGGAC CCCCTTCACT                                              20

(2) INFORMATION FOR SEQ ID NO: 11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

AARGTYGGWT TYTTYAAR                                                18

(2) INFORMATION FOR SEQ ID NO: 12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GAAATHGAYG AYTTRATG                                                18
```